US008309072B2

(12) United States Patent
Zhabilov

(10) Patent No.: US 8,309,072 B2
(45) Date of Patent: *Nov. 13, 2012

(54) IRREVERSIBLY-INACTIVATED PEPSINOGEN FRAGMENTS FOR MODULATING IMMUNE FUNCTION

(75) Inventor: Harry H. Zhabilov, San Marino, CA (US)

(73) Assignee: The Zhabilov Trust, San Marino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/487,637

(22) Filed: Jun. 18, 2009

(65) Prior Publication Data

US 2009/0285776 A1 Nov. 19, 2009

Related U.S. Application Data

(63) Continuation-in-part of application No. 12/315,441, filed on Dec. 2, 2008, now Pat. No. 8,067,531, and a continuation-in-part of application No. 12/321,262, filed on Jan. 16, 2009, now Pat. No. 8,066,982.

(60) Provisional application No. 60/626,882, filed on Nov. 12, 2004, provisional application No. 60/635,938, filed on Dec. 15, 2004.

(51) Int. Cl.
*A01N 63/00* (2006.01)
*A61K 38/00* (2006.01)

(52) U.S. Cl. ........................... 424/93.1; 530/300

(58) Field of Classification Search ............... None
See application file for complete search history.

(56) References Cited

U.S. PATENT DOCUMENTS

| | | | |
|---|---|---|---|
| 4,534,966 A | 8/1985 | Ohnishi et al. | |
| 5,002,766 A | 3/1991 | Ransberger et al. | |
| 5,436,143 A | 7/1995 | Hyman | |
| 5,872,210 A | 2/1999 | Medabalimi | |
| 6,165,794 A | 12/2000 | Craik et al. | |
| 6,461,615 B1 | 10/2002 | Srivastava | |
| 6,534,310 B1 | 3/2003 | Craik et al. | |
| 6,719,974 B1 | 4/2004 | Rothman et al. | |
| 6,979,566 B2 | 12/2005 | Friedman et al. | |
| 7,479,538 B2 * | 1/2009 | Zhabilov | 530/327 |
| 8,066,982 B2 * | 11/2011 | Zhabilov | 424/93.1 |
| 2002/0192797 A1 | 12/2002 | Dash et al. | |
| 2004/0005557 A1 | 1/2004 | Padigaru et al. | |
| 2004/0038330 A1 | 2/2004 | Nagaoka | |
| 2009/0175838 A1 | 7/2009 | Newell et al. | |
| 2010/0034839 A1 | 2/2010 | Newell et al. | |

FOREIGN PATENT DOCUMENTS

| | | |
|---|---|---|
| AU | 678202 B | 12/1995 |
| WO | WO/2007/041285 | 12/2007 |

OTHER PUBLICATIONS

Litwin et al. Uint. Arch Allergy Appl. Immunol. 1988, vol. 87, pp. 361-366.*

Srivastava, P. (2002). Interactions of heat shock proteins with peptides and antigen presenting cells Annu. Rev. immunol. 20: 395-425.

Suzue K. and Young RA. Heat shock proteins as immunological carriers and vaccines. PubMed PMID 8856990. In: Stress-inducible Cellular Response, ed. U. Fiege, Birkhauser (1996) 77: 451-465.

Murray P. and Young RA. Stress and Immunological recognition in host-pathogen interaction. ,J Bacteriol (1992) vol. 174, No. 13, p. 4193-4196.

Suto, R. and Srivastava, P.K 1995. A mechanism for the specific immunogenicity of heat shock protein-chaperoned peptides. Science (1995) Sep. 15; 269; 1585-8.

Vabulas, R. M., Wagner, H. and Schild, H. (2002). Heat shock proteins as ligands of toll-like receptors. Curr. Topics Microbiol.Immunol. 270; 169.

Sigal TJ., Crotty S., Andino R. and Rock KL. Cytotoxic T-cell immunity to virus-infected non-haematopoietic cell requires presentation of exogenous antigen. Nature (1999) 398:77 80.

Derky CS. Task force on recurrent respiratory papillomatosis. Arch Otolaryngol Head Neck Surg (1995) 121: 1386-1391.

Panjwani, N. N., Popova, L, Febbraio, M and Srivastava, P. K. (2001) CD91 is common receptor for heat shock proteins gp96, HSP 90, HSP70 and calreticulin. Immunity 14:303.

Srivastava, P. K., Deleo, A. B. and Old, L. J. Tumor rejection antigens of chemically induced sarcomas of inbred mice. Proc. Nat. Acad. Sci. USA. vol. 83:3407-11 May 1986.

Pockley, G. A. (2001) Heat Shock proteins in health and disease: therapeutic targets or therapeutic agents? Exp. Rev. Mol. Med. Sep. 21, http://www.ermm.cbcu.cam.ac.uk/01003556h.htm.

Parmiani, G. et al., (2004) Heat Shock Proteins and Their Use as Anticancer Vaccines. Clinical Cancer Research. vol. 10, 8142-8146. Dec 15.

Gritti, I., Banfi, G., and Roi, G.S., Pepsinogens: Physiology, Pharmacology Pathophysiology and Exercise. (2000) Pharmacological Research. vol. 41. Nov 3.

GP96 Heat Shock Protein-Peptide Complex Vaccine in Treating Patients With Recurrent or Progressive Glioma, National Cancer Institute, Jun. 2009.

(Continued)

*Primary Examiner* — Bao Li
(74) *Attorney, Agent, or Firm* — Cislo & Thomas, LLP

(57) ABSTRACT

Isolated anti-cancer peptides are disclosed which are characterized by the amino acid sequences TLTSGGGAIALPPS-MAAPPLGPVAPLTGAIHAPTXG (SEQ ID NO: 1); TLSTATGGAIPPVAAMPPGLVAPTHGPAIHP (SEQ ID NO: 2); CCATSGPCGAVMILTPHLTA (SEQ ID NO: 5); MTLTTGSGAIAPAMPPGLPPHTGAIHAPM (SEQ ID NO: 4); and NXVPVSVEGYXQITLDSITX (SEQ ID NO: 3) and a significant in vitro binding affinity for gp96. The peptides exhibit anti-tumor, anti-cancer activity in vivo. Also disclosed is an isolated antiviral peptide characterized by the amino acid sequence GDEPLENYLDTEYF (SEQ ID NO: 6) and a significant in vitro binding affinity for HIV-1 gp 120 and gp 41, and human CD4 cells. The peptide exhibits anti-retroviral activity in vivo, particularly anti-HIV-1 activity.

3 Claims, 20 Drawing Sheets

OTHER PUBLICATIONS

Rebecca L. O'Brien et al., "Heat Shock Protein Hsp60-reactive cells: A Large, Diversified T-lymphocyte Subset with Highly Focused Specificity" 5 pgs, Jan. 2, 1992.

U.S. Appl. No. 11/973,920, filed Nov. 26, 2009, Agadjanyan et al.

Sogawa K et al. "Molecular Cloning of Complementary DNA to Swine Pesinogen Messenger RNA", Journal of Biological Chemistry, vol. 256, No. 23, 1981, pp. 12561-12565.

Tanaka T et al.: "N-terminal portion acts as an initiator of the inactivation of pepsin at neutral pH." Protein Engineering Sep. 2001, p. 669-675, vol. 14, No. 9.

Jiang S et al.: "Peptide and Non-Peptide HIV Fusion INhibitors" Current Pharmacutical Design, Bentham Science Publishers, vol. 8, No. 8, Jan. 2002, p. 563-580.

Yu F.I. et al.: "Fluorogenic Peptide Substrates for Assay for Asparty Proteinases" Analytical Biochemistry. vol. 234, Mar. 1996, pp. 113-188.

Supplementary European Search Report, EP 05 85 0002, Oct. 1, 2010.

U.S. Appl. No. 10/336,512, filed Jan. 29, 2004, Zhabilov.

Lin, X-L, et al. Synthesis, Purification and Active Site Mutagenesis of Recombinant Porcine Pepsinogen, J. Biolog. Chem. Mar. 15, 1989, pp. 4482-4489, vol. 264, No. 8.

Filippova, I. et al. Fluorogenic Peptide Substrates for Assay of Asparty Proteinases, Analytical Biochemistry, Mar. 1996, pp. 113-118. vol. 234.

Pockley, A. Heat Shock Proteins in Health and Disease: Theraputic Targets or Theraputic Agents?. Expert Reviews in Molucular Medicine. Sep. 21, 2001.

Sreedhar, A. et al. Heal Shock Proteins in the Regulation of Apoptosis: New Strategies in Tumor ... Pharmacology & Therapeutics. Mar. 2004, pp. 227-257, vol. 101, No. 3.

Kamatari et al. Structural Dissection of Alkaline-denatured Pepsin. Science. 2003, pp. 717-724, vol. 12.

Campos et al. The Active Site of Pepsin is Formed in the Intermediate Conformation Dominant at Mildly Acidic pH. FEBS Letters. 2003. pp. 89-95, vol. 538.

Harlow, E. et al. Antibodies: A Laboratory Manual, 1988, pp. 626-628, Cold Springs Harbor, NY.

Boyd, M.R. AIDS Etiology: Diagnosis, Treatment, and Prevention. Lippincott. 1988, pp. 305-319.

Sigal, L. et al. Cytotoxic T-cell Immunity to Wire-Infected Non-haematic Cells ..., Nature, 1999, pp. 77-80, Issue 398.

Gulakowski, R., Laboratory of Drug Discovery Research and Development, Journal of Virological Methods, Jun. 1991. pp. 87-100, vol. 33, No. 1-2.

Tang. J. et al., Amino-Acid Sequence of Porcine Pepsin, Proceedings of The National Academy of Sciences. Dec. 1973, pp. 3437-3439, vol. 70, No. 12.

Weissenhorn, W. et al., Atomic Structure of the Ectodomain from HIV-1 gp41, Nature, May 22, 1997, pp. 426-430, No. 387.

Kirk, R., et al., A Nonpromoting Phorbol from Samoan Medicinal Plant Homalanthus Nutans ..., Journal of Medicinal Chemistry, 1992, pp. 1978-1986, vol. 35, No. 11.

Moore, J. et al., HIV Envelope's Letters Boxed into Shape. Nature. Jun. 18, 1998, pp. 630-631, No. 393.

Weislow, O. et al., New Sotuable-formazan Assay for HIV-1 Cytopathic Effects ..., Journal of the National Cancer Institute, Jun. 21, 1989, p. 963, vol. 81, No. 12.

Laemmli, U., Cleavage of Structural Proteins During the Assembly of the Head Etaciertophage T4, Nature, Aug. 15, 1970. pp. 684-685.

Pockley, A., Heat Shock Proteins in Health and Disease ... (Figure 4), Expert Reviews in Molecular Medicine, Sep. 21, 2001.

Radsak, M., The Heat Shock Protein Gp96 Binds to Human Neutrophils and Monocytes and Stimmulates Effector Functions, Blood. Apr. 1, 2003. pp. 2810-2815, vol. 101, No. 7.

Weissenhorn, W., Structural Basis for Membrane Fusion by Envelope Viruses, Molecular Membrane Biology, Jan. 1, 1999, pp. 3-9, vol. 1, No. 1.

Yu. I. et al. Flurogenic Peptide Substrates for Assay of Asparty Proteinases. Analytical Biochemistry, Mar. 1996, vol. 234, pp. 113-118.

Finn, Olivera. Cancer Vaccines: Between the Idea and the Reality. Nature Publishing Group, Aug. 2003. vol. 3, pp. 630-641.

Pilcher, Christopher. T-20 and Beyond: Inhibition of HIV Attachment and Fusion at the 9th CROI. 9th Conf on Retroviruses & Opportunistic Infections, Feb. 2002. Seattle WA.

Greenberg, ML et al. Virus Sensitivity T-20 and T-1249 is Independent of Coreceptor Usage. 8th Conf on Retroviruses & Opportunistic Infections. Feb. 2001, Chicago III.

* cited by examiner

Porcine pepsinogen sequence:

MKWLLLLSLV VLSECLVKVP LVRKKSLRQN LIKNGKLKDF LKTHKHNPAS KYFPEAAALI GDEPLENYLD | Pig
                                                                IGDEPLENYLD | Pig

TEYFGTIGIG TPAQDFTVIF DTGSSNLWVP SVYCSSLACS DHNQFNPDDS STFEATSQEL SITYGTGSMT | Pig
TEYF-45K IPF-PI

GILGYDTVQV GGISDTNQIF GLSETEPGSF LYYAPFDGIL GLAYPSISAS GATPVFDNLW DQGLVSQDLF | Pig
                                                          S GATPZTE -30K CP

SVYLSSNDDS GSVVLLGGID SSYYTGSLNW VPVSVEGYWQ ITLDSITMDG ETIACSGGCQ AIVDTGTSLL | Pig
                                       NX VPVSVEGYXQ ITLDSITX-15K IPF-PI
                            LGGID   SSYYTGSLNW VPVSVEGYWQ IT-20K CP
                                    SYYTGSLNWR VPVSVEGYWQ ITLDSITM-20K CP
                                    SYYTGSLNW  VPVSVEGYWQ ITLDSI-15K CP
                                    NW         VPVSVEGYWQ ITLDSITMDG RTI-15K CPL

TGPTSAIAIN IQDSIGASEN SDGEMVISCS SIDSLPDIVF TINGVQYPLS PSAYILQDDD SCTSGFEGMn | Pig

VPTSSGELWI LGDVFIRQY TVFDRANNKV GLAPVA. | Pig

GDEPLENYLIDTEW--from 45 kDa band of IPF-P i prep
NXVPVSVEGYXQITLDSITX-from 15 kDa band of IPF-PI prep
SGATPVF-30K CP [CUP]
LGGII7SSYYTGSLNWPVSVEGYWQIT--20K CP (primary sequence)
SYYTGSLNW/PVSVEGYWQITLDSITM--20K CP (minor sequence)
SAYTGSLNW/PVSVEGYWQITLDSI--15K CP (primary sequence)
NWVPVSVEGYWQITLDSITMDGRTI--15K CP (minor sequence)

FIG. 1

Amino Acid Normalization

| Amino Acid | aas350 | nmoles aa | Sample: % loaded: MW: | µgrams | IPF 25% 45,000 mole percent | of 6 ul # residues |
|---|---|---|---|---|---|---|
| cys&0 | | | | | | |
| cmcys | | | | | | |
| asx | 22.8877 | 22.888 | | 2.634 | 12.0% | 52.4 |
| thr | 12.4691 | 12.469 | | 1.261 | 6.5% | 28.6 |
| ser | 18.8294 | 18.829 | | 1.640 | 9.8% | 43.1 |
| glx | 17.3625 | 17.363 | | 2.224 | 9.1% | 39.8 |
| pro+cys | 14.1223 | 14.122 | | 1.372 | 7.4% | 32.3 |
| gly | 30.3407 | 30.341 | | 1.731 | 15.9% | 69.5 |
| ala | 11.6158 | 11.616 | | 0.828 | 6.1% | 26.6 |
| val | 11.7925 | 11.793 | | 1.169 | 6.2% | 27.0 |
| met | 2.0077 | 2.008 | | 0.263 | 1.1% | 4.6 |
| ileu | 12.4681 | 12.468 | | 1.413 | 6.5% | 28.6 |
| leu | 13.8494 | 13.849 | | 1.567 | 7.2% | 31.7 |
| tyr | 8.7045 | 8.705 | | 1.420 | 4.6% | 19.9 |
| phe | 7.6838 | 7.684 | | 1.132 | 4.0% | 17.6 |
| his | 1.5271 | 1.527 | | 0.209 | 0.8% | 3.5 |
| lys | 2.6238 | 2.624 | | 0.336 | 1.4% | 6.0 |
| trp | | | | | | |
| arg | 2.8688 | 2.869 | | 0.448 | 1.5% | 6.6 |
| % injected 100% | | | | | total residues: | 438 |

|  | nmol protein | µg |
|---|---|---|
| Analyzed | 0.436 | 19.647 |
| Sample total | 1.7464 | 78.588 |

(w/o Cys, Trp)

```
SAMPLE NAME:      I

THR
                  LEU
                  TYR
                  SER
                  GLY           SER
                  GLU   ARG    MET
                  GLN   LYS    ASN   PHE         PRO   PHE
                  ASP   PHE    ASP   LEU   VAL   LEU               ASN   HIS
SEQUENCE:         ILE  -PRO   -PRO  -GLU  -ASP- TYR  -GLY  -ILE  - ALA -
CYCLE #:           1     2      3     4     5     6     7     8     9

MET
SEQUENCE:         PHE - THR - X -   GLY
CYCLE #:           10    11    12   13

YIELD (pmol):  GLU (4)    342.49   YIELD (pmol):   ASP(5)    257.55

CARRYOVER:     GLU (4)    10.1%    PERCENT LOADED: 1UL

SEQSTD YIELD:  NL (6)     3.10     SEQSTD CARRYOVER: NL (6)   14.2%

SEQSTD REP YIELD:    NL(6,11)          81.4%

COMMENTS:         COMPLEX MIXTURE. AMINO ACIDS INTERCHANGEABLE AT
                  MOST CYCLES. LEVEL OF SEQUENCING DROPPED OFF
                  AFTER CYCLE 5. VARIOUS COMBINATIONS OF AMINO
                  ACIDS HAVE SIMILARITY WITH PORCINE PEPSIN

PINK HIGHLIGHTED AMINO ACIDS: RESIDUES 20-22
                  ORANGE HIGHLIGHTED AMINO ACIDS: RESIDUES 63-75
                  BLUE HIGHLIGHTED AMINO ACIDS: RESIDUES 32-37
                  GREEN HIGHLIGHTED AMINO ACIDS: RESIDUES 60-67
                  PURPLE HIGHLIGHTED AMINO ACIDS: RESIDUES 100-103
                  YELLOW HIGHLIGHTED AMINO ACIDS: RESIDUES 222-229
```

Figure 11

SAMPLE NAME:    P

```
                THR
                LEU
                SER
                TRP
                ALA
                TYR
                GLN
                °GLU
                GLY        GASP
                ASP   PHE  ASN   PHE        PHE         PRO
                GILE  °PRO  MET  PGLU  PVAL °TYR        GASN
SEQUENCE:       X  -  PVAL -PPRO- YLEU -ASP- PHIS -GLY - ILE - HIS -
CYCLE #:        1     2     3     4    5    6    7     8     9

SEQUENCE:       PHE
CYCLE #:        10
```

YIELD (pmol):   ILE (1)   1810.70   YIELD (pmol):    VAL(2) 339.92.55

CARRYOVER:      VAL (5)      18.3%      REP YIELD: VAL(2,5) 85.9%

PERCENT LOADED: 1 UL

SEQSTD YIELD:   NL (6)       1.32   SEQSTD CARRYOVER:  NL (6)     41.7%

SEQSTD REP YIELD:       NL(6,11)          85.7%

COMMENTS:       MIXTURE WITH AMINO ACIDS INTERCHANGEABLE AT MOST
                CYCLES. VARIOUS COMBINATIONS OF AMINO ACIDS HAVE
                SIMILARITY WITH PORCINE PEPSIN

YELLOW  HIGHLIGHTED AMINO ACIDS: RESIDUES 19-21
                GREEN HIGHLIGHTED AMINO ACIDS: RESIDUES 60-67
                ORANGE HIGHLIGHTED AMINO ACIDS: RESIDUES 63-68
                PINK HIGHLIGHTED AMINO ACIDS: RESIDUES 98-103

Figure 12

| | Immobilized Target | | | | | |
|---|---|---|---|---|---|---|
| | IPF | CD4 | Gp41 (short) | Gp120 | Gp41 (long) | H-Serum (M) |
| IPF | | Yes. Fig.15 Fig.18 | Yes. Fig.16 Fig.18 | Yes. Fig.17 Fig.18 | No | Yes. Fig.20 |
| CD4 | Yes?? Fig.14 | | | | | |
| Gp41 (short) | No | | | | | |
| Gp120 | No | | | | | |
| Gp41 (long) | No | | | | | |
| H-Serum (M) | Yes. Fig.19 | | | | | |

Soluble Ligand

FIG. 13

SEQUENCE LISTING

```
<160> NUMBER OF SEQ ID NOS: 33

<210> SEQ ID NO 1
<211> LENGTH: 36
<212> TYPE: PRT
<213> ORGANISM: Sus scrofa
<220> FEATURE:
<221> NAME/KEY: misc_feature
<222> LOCATION: (35)..(35)
<223> OTHER INFORMATION: Xaa can be any naturally occurring amino acid

<400> SEQUENCE: 1

Thr Leu Thr Ser Gly Gly Gly Ala Ile Ala Leu Pro Pro Ser Met Ala
1               5                   10                  15

Ala Pro Pro Leu Gly Pro Val Ala Pro Leu Thr Gly Ala Ile His Ala
            20                  25                  30

Pro Thr Xaa Gly
        35

<210> SEQ ID NO 2
<211> LENGTH: 31
<212> TYPE: PRT
<213> ORGANISM: Sus scrofa

<400> SEQUENCE: 2

Thr Leu Ser Thr Ala Thr Gly Gly Ala Ile Pro Pro Val Ala Ala Met
1               5                   10                  15

Pro Pro Gly Leu Val Ala Pro Thr His Gly Pro Ala Ile His Pro
            20                  25                  30

<210> SEQ ID NO 3
<211> LENGTH: 20
<212> TYPE: PRT
<213> ORGANISM: Sus scrofa
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
```

-continued

<400> SEQUENCE: 3

Asn Xaa Val Pro Val Ser Val Glu Gly Tyr Xaa Gln Ile Thr Leu Asp
1               5                   10                  15

Ser Ile Thr Xaa
            20

<210> SEQ ID NO 4
<211> LENGTH: 29
<212> TYPE: PRT
<213> ORGANISM: Sus scrofa

<400> SEQUENCE: 4

Met Thr Leu Thr Thr Gly Ser Gly Ala Ile Ala Pro Ala Met Pro Pro
1               5                   10                  15

Gly Leu Pro Pro His Thr Gly Ala Ile His Ala Pro Met
            20                  25

<210> SEQ ID NO 5
<211> LENGTH: 20
<212> TYPE: PRT
<213> ORGANISM: Sus scrofa

<400> SEQUENCE: 5

Cys Cys Ala Thr Ser Gly Pro Cys Gly Ala Val Met Ile Leu Thr Pro
1               5                   10                  15

His Leu Thr Ala
            20

<210> SEQ ID NO 6
<211> LENGTH: 14
<212> TYPE: PRT
<213> ORGANISM: Sus scrofa

<400> SEQUENCE: 6

Gly Asp Glu Pro Leu Glu Asn Tyr Leu Asp Thr Glu Tyr Phe
1               5                   10

<210> SEQ ID NO 7
<211> LENGTH: 386
<212> TYPE: PRT
<213> ORGANISM: Sus scrofa

<400> SEQUENCE: 7

Met Lys Trp Leu Leu Leu Ser Leu Val Val Leu Ser Glu Cys Leu
1               5                   10                  15

Val Lys Val Pro Leu Val Arg Lys Lys Ser Leu Arg Gln Asn Leu Ile
            20                  25                  30

Lys Asn Gly Lys Leu Lys Asp Phe Leu Lys Thr His Lys His Asn Pro
        35                  40                  45

Ala Ser Lys Tyr Phe Pro Glu Ala Ala Ala Leu Ile Gly Asp Glu Pro
    50                  55                  60

Leu Glu Asn Tyr Leu Asp Thr Glu Tyr Phe Gly Thr Ile Gly Ile Gly
65                  70                  75                  80

Thr Pro Ala Gln Asp Phe Thr Val Ile Phe Asp Thr Gly Ser Ser Asn
                85                  90                  95

Leu Trp Val Pro Ser Val Tyr Cys Ser Ser Leu Ala Cys Ser Asp His
            100                 105                 110

Asn Gln Phe Asn Pro Asp Asp Ser Ser Thr Phe Glu Ala Thr Ser Gln
        115                 120                 125

```
Glu Leu Ser Ile Thr Tyr Gly Thr Gly Ser Met Thr Gly Ile Leu Gly
    130                 135                 140

Tyr Asp Thr Val Gln Val Gly Gly Ile Ser Asp Thr Asn Gln Ile Phe
145                 150                 155                 160

Gly Leu Ser Glu Thr Glu Pro Gly Ser Phe Leu Tyr Tyr Ala Pro Phe
                165                 170                 175

Asp Gly Ile Leu Gly Leu Ala Tyr Pro Ser Ile Ser Ala Ser Gly Ala
                180                 185                 190

Thr Pro Val Phe Asp Asn Leu Trp Asp Gln Gly Leu Val Ser Gln Asp
            195                 200                 205

Leu Phe Ser Val Tyr Leu Ser Ser Asn Asp Asp Ser Gly Ser Val Val
210                 215                 220

Leu Leu Gly Gly Ile Asp Ser Ser Tyr Tyr Thr Gly Ser Leu Asn Trp
225                 230                 235                 240

Val Pro Val Ser Val Glu Gly Tyr Trp Gln Ile Thr Leu Asp Ser Ile
                245                 250                 255

Thr Met Asp Gly Glu Thr Ile Ala Cys Ser Gly Gly Cys Gln Ala Ile
                260                 265                 270

Val Asp Thr Gly Thr Ser Leu Leu Thr Gly Pro Thr Ser Ala Ile Ala
            275                 280                 285

Ile Asn Ile Gln Ser Asp Ile Gly Ala Ser Glu Asn Ser Asp Gly Glu
            290                 295                 300

Met Val Ile Ser Cys Ser Ser Ile Asp Ser Leu Pro Asp Ile Val Phe
305                 310                 315                 320

Thr Ile Asn Gly Val Gln Tyr Pro Leu Ser Pro Ser Ala Tyr Ile Leu
                325                 330                 335

Gln Asp Asp Asp Ser Cys Thr Ser Gly Phe Glu Gly Met Asp Val Pro
                340                 345                 350

Thr Ser Ser Gly Glu Leu Trp Ile Leu Gly Asp Val Phe Ile Arg Gln
            355                 360                 365

Tyr Tyr Thr Val Phe Asp Arg Ala Asn Asn Lys Val Gly Leu Ala Pro
    370                 375                 380

Val Ala
385

<210> SEQ ID NO 8
<211> LENGTH: 9
<212> TYPE: PRT
<213> ORGANISM: Sus scrofa

<400> SEQUENCE: 8

Thr Leu Tyr Ser Gly Glu Gln Asp Ile
1               5

<210> SEQ ID NO 9
<211> LENGTH: 4
<212> TYPE: PRT
<213> ORGANISM: Sus scrofa

<400> SEQUENCE: 9

Arg Lys Phe Pro
1

<210> SEQ ID NO 10
<211> LENGTH: 5
<212> TYPE: PRT
<213> ORGANISM: Sus scrofa
```

```
<400> SEQUENCE: 10

Ser Met Asn Asp Pro
1               5

<210> SEQ ID NO 11
<211> LENGTH: 70
<212> TYPE: PRT
<213> ORGANISM: Sus scrofa

<400> SEQUENCE: 11

Met Lys Trp Leu Leu Leu Ser Leu Val Leu Ser Glu Cys Leu
1               5                   10                  15

Val Lys Val Pro Leu Val Arg Lys Lys Ser Leu Arg Gln Asn Leu Ile
            20                  25                  30

Lys Asn Gly Lys Leu Lys Asp Phe Leu Lys Thr His Lys His Asn Pro
        35                  40                  45

Ala Ser Lys Tyr Phe Pro Glu Ala Ala Ala Leu Ile Gly Asp Glu Pro
    50                  55                  60

Leu Glu Asn Tyr Leu Asp
65                  70

<210> SEQ ID NO 12
<211> LENGTH: 11
<212> TYPE: PRT
<213> ORGANISM: Sus scrofa

<400> SEQUENCE: 12

Ile Gly Asp Glu Pro Leu Glu Asn Tyr Leu Asp
1               5                   10

<210> SEQ ID NO 13
<211> LENGTH: 70
<212> TYPE: PRT
<213> ORGANISM: Sus scrofa

<400> SEQUENCE: 13

Thr Glu Tyr Phe Gly Thr Ile Gly Ile Gly Thr Pro Ala Gln Asp Phe
1               5                   10                  15

Thr Val Ile Phe Asp Thr Gly Ser Ser Asn Leu Trp Val Pro Ser Val
            20                  25                  30

Tyr Cys Ser Ser Leu Ala Cys Ser Asp His Asn Gln Glu Asn Pro Asp
        35                  40                  45

Asp Ser Ser Thr Phe Glu Ala Thr Ser Gln Glu Leu Ser Ile Thr Tyr
    50                  55                  60

Gly Thr Gly Ser Met Thr
65                  70

<210> SEQ ID NO 14
<211> LENGTH: 4
<212> TYPE: PRT
<213> ORGANISM: Sus scrofa

<400> SEQUENCE: 14

Thr Glu Tyr Phe
1

<210> SEQ ID NO 15
<211> LENGTH: 70
<212> TYPE: PRT
<213> ORGANISM: Sus scrofa
```

-continued

<400> SEQUENCE: 15

Gly Ile Leu Gly Tyr Asp Thr Val Gln Val Gly Gly Ile Ser Asp Thr
1               5                   10                  15

Asn Gln Ile Phe Gly Leu Ser Glu Thr Glu Pro Gly Ser Phe Leu Tyr
            20                  25                  30

Tyr Ala Pro Phe Asp Gly Ile Leu Gly Leu Ala Tyr Pro Ser Ile Ser
        35                  40                  45

Ala Ser Gly Ala Thr Pro Val Phe Asp Asn Leu Trp Asp Gln Gly Leu
    50                  55                  60

Val Ser Gln Asp Leu Phe
65                  70

<210> SEQ ID NO 16
<211> LENGTH: 8
<212> TYPE: PRT
<213> ORGANISM: Sus scrofa

<400> SEQUENCE: 16

Ser Gly Ala Thr Pro Glx Thr Glu
1               5

<210> SEQ ID NO 17
<211> LENGTH: 70
<212> TYPE: PRT
<213> ORGANISM: Sus scrofa

<400> SEQUENCE: 17

Ser Val Tyr Leu Ser Ser Asn Asp Asp Ser Gly Ser Val Val Leu Leu
1               5                   10                  15

Gly Gly Ile Asp Ser Ser Tyr Tyr Thr Gly Ser Leu Asn Trp Val Pro
            20                  25                  30

Val Ser Val Glu Gly Tyr Trp Gln Ile Thr Leu Asp Ser Ile Thr Met
        35                  40                  45

Asp Gly Glu Thr Ile Ala Cys Ser Gly Gly Cys Gln Ala Ile Val Asp
    50                  55                  60

Thr Gly Thr Ser Leu Leu
65                  70

<210> SEQ ID NO 18
<211> LENGTH: 20
<212> TYPE: PRT
<213> ORGANISM: Sus scrofa
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 18

Asn Xaa Val Pro Val Ser Val Glu Gly Tyr Xaa Gln Ile Thr Leu Asp
1               5                   10                  15

Ser Ile Thr Xaa
            20

```
<210> SEQ ID NO 19
<211> LENGTH: 25
<212> TYPE: PRT
<213> ORGANISM: Sus scrofa

<400> SEQUENCE: 19

Leu Gly Gly Ile Asp Ser Ser Tyr Tyr Thr Gly Ser Leu Asn Trp Val
1               5                   10                  15

Pro Val Ser Val Glu Gly Tyr Trp Gln
            20                  25

<210> SEQ ID NO 20
<211> LENGTH: 28
<212> TYPE: PRT
<213> ORGANISM: Sus scrofa

<400> SEQUENCE: 20

Ser Tyr Tyr Thr Gly Ser Leu Asn Ile Arg Val Pro Val Ser Val Glu
1               5                   10                  15

Gly Tyr Trp Gln Ile Thr Leu Asp Ser Ile Thr Met
            20                  25

<210> SEQ ID NO 21
<211> LENGTH: 25
<212> TYPE: PRT
<213> ORGANISM: Sus scrofa

<400> SEQUENCE: 21

Ser Tyr Tyr Thr Gly Ser Leu Asn Trp Val Pro Val Ser Val Glu Gly
1               5                   10                  15

Tyr Trp Gln Ile Thr Leu Asp Ser Ile
            20                  25

<210> SEQ ID NO 22
<211> LENGTH: 25
<212> TYPE: PRT
<213> ORGANISM: Sus scrofa

<400> SEQUENCE: 22

Asn Trp Val Pro Val Ser Val Glu Gly Tyr Trp Gln Ile Thr Leu Asp
1               5                   10                  15

Ser Ile Thr Met Asp Gly Arg Thr Ile
            20                  25

<210> SEQ ID NO 23
<211> LENGTH: 70
<212> TYPE: PRT
<213> ORGANISM: Sus scrofa

<400> SEQUENCE: 23

Thr Gly Pro Thr Ser Ala Ile Ala Ile Asn Ile Gln Ser Asp Ile Gly
1               5                   10                  15

Ala Ser Glu Asn Ser Asp Gly Glu Met Val Ile Ser Cys Ser Ser Ile
            20                  25                  30

Asp Ser Leu Pro Asp Ile Val Phe Thr Ile Asn Gly Val Gln Tyr Pro
        35                  40                  45

Leu Ser Pro Ser Ala Tyr Ile Leu Gln Asp Asp Ser Cys Thr Ser
    50                  55                  60

Gly Phe Glu Gly Asn Met
65                  70
```

```
<210> SEQ ID NO 24
<211> LENGTH: 36
<212> TYPE: PRT
<213> ORGANISM: Sus scrofa

<400> SEQUENCE: 24

Val Pro Thr Ser Ser Gly Glu Leu Trp Ile Leu Gly Asp Val Phe Ile
1               5                   10                  15

Arg Gln Tyr Tyr Thr Val Phe Asp Arg Ala Asn Asn Lys Val Gly Leu
            20                  25                  30

Ala Pro Val Ala
        35

<210> SEQ ID NO 25
<211> LENGTH: 14
<212> TYPE: PRT
<213> ORGANISM: Sus scrofa

<400> SEQUENCE: 25

Gly Asp Glu Pro Leu Glu Asn Tyr Leu Ile Asp Thr Glu Trp
1               5                   10

<210> SEQ ID NO 26
<211> LENGTH: 20
<212> TYPE: PRT
<213> ORGANISM: Sus scrofa
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 26

Asn Xaa Val Pro Val Ser Val Glu Gly Tyr Xaa Gln Ile Thr Leu Asp
1               5                   10                  15

Ser Ile Thr Xaa
        20

<210> SEQ ID NO 27
<211> LENGTH: 7
<212> TYPE: PRT
<213> ORGANISM: Sus scrofa

<400> SEQUENCE: 27

Ser Gly Ala Thr Pro Val Phe
1               5

<210> SEQ ID NO 28
<211> LENGTH: 27
<212> TYPE: PRT
<213> ORGANISM: Sus scrofa

<400> SEQUENCE: 28

Leu Gly Gly Ile Ile Ser Ser Tyr Tyr Thr Gly Ser Leu Asn Trp Val
1               5                   10                  15

Pro Val Ser Val Glu Gly Tyr Trp Gln Ile Thr
            20                  25
```

```
<210> SEQ ID NO 29
<211> LENGTH: 27
<212> TYPE: PRT
<213> ORGANISM: Sus scrofa

<400> SEQUENCE: 29

Ser Tyr Tyr Thr Gly Ser Leu Asn Trp Val Pro Val Ser Val Glu Gly
1               5                   10                  15

Tyr Trp Gln Ile Thr Leu Ser Asp Ile Thr Met
            20                  25

<210> SEQ ID NO 30
<211> LENGTH: 25
<212> TYPE: PRT
<213> ORGANISM: Sus scrofa

<400> SEQUENCE: 30

Ser Ala Tyr Thr Gly Ser Leu Asn Trp Val Pro Val Ser Val Glu Gly
1               5                   10                  15

Tyr Trp Gln Ile Thr Leu Asp Ser Ile
            20                  25

<210> SEQ ID NO 31
<211> LENGTH: 25
<212> TYPE: PRT
<213> ORGANISM: Sus scrofa

<400> SEQUENCE: 31

Asn Trp Val Pro Val Ser Val Glu Gly Tyr Trp Gln Ile Thr Leu Asp
1               5                   10                  15

Ser Ile Thr Met Asp Gly Arg Thr Ile
            20                  25

<210> SEQ ID NO 32
<211> LENGTH: 12
<212> TYPE: PRT
<213> ORGANISM: Sus scrofa
<220> FEATURE:
<221> NAME/KEY: misc_feature
<222> LOCATION: (12)..(12)
<223> OTHER INFORMATION: Xaa can be any naturally occurring amino acid

<400> SEQUENCE: 32

Tyr Leu Ser Trp Ala Tyr Gln Glu Gly Asp Ile Xaa
1               5                   10

<210> SEQ ID NO 33
<211> LENGTH: 4
<212> TYPE: PRT
<213> ORGANISM: Sus scrofa

<400> SEQUENCE: 33

Asp Asn Met Pro
1
```

IRREVERSIBLY-INACTIVATED PEPSINOGEN FRAGMENTS FOR MODULATING IMMUNE FUNCTION

CROSS-REFERENCE TO RELATED APPLICATIONS

This utility patent application is a continuation-in-part application of, and claims priority from application Ser. Nos. 12/315,441 and 12/321,262, filed respectively on Dec. 2, 2008 now U.S. Pat. No. 8,067,531 and Jan. 16, 2009, now U.S. Pat. No. 8,066,982 which in turn claim priority from U.S. Pat. No. 7,479,538, filed on Jul. 11, 2005 and entitled "Irreversibly-inactivated Pepsinogen Fragment and Pharmaceutical Compositions Comprising the Same for Detecting, Preventing, and Treating HIV", which in turn claims priority from Provisional Application Nos. 60/626,882 and 60/635,938 filed on, respectively, Nov. 12, 2004 and Dec. 15, 2004, the disclosures of which are incorporated herein in their entireties by this reference.

FIELD OF THE INVENTION

The present invention relates to compositions and methods comprising an inactivated pepsin fragment ("IPF") for modulating immune system activity. More specifically, embodiments of the present invention are directed to compositions and methods to elicit specific immunity to recognize peptides associated with tumors and malignancies. The present invention also relates to compositions and methods comprising IPF for treating infections such as infection by the human immunodeficiency virus.

BACKGROUND OF THE INVENTION

Current studies indicate that immune protection against cancer requires the generation of a potent cellular immune response against a unique tumor antigen expressed by a malignant cell. Thus, successful immune protection would first require identifying a unique antigen in the tumor cells (tumor specific antigen) and then inducing a potent T-cell response targeted to the tumor antigen. These tumor-associated antigens, however, would still be recognized by immune cells as 'self' molecules, and so no true activation of the immune system would occur. Thus, two obstacles in targeting these tumor-associated molecules as a vaccine include the unresponsiveness of the immune system to 'self' molecules, which restricts its ability to generate potent cellular immune responses, and preventing the generated immune response from being directed to normal cells that express the target antigen.

Proteins that show promise in overcoming these problems include heat shock proteins (HSPs). HSPs include a collection of ubiquitously expressed cytoprotective proteins, which are expressed by cells under conditions of cell stress, such as increased temperature, viral infection and oxidative stress. Certain HSPs have been shown to have immunomodulatory effects, such as the induction of cytokines and the promotion of cell activation and maturation (see, Pockley A G, Lancet 363 (9382) 469-476 (2003)).

Gp96 is an HSP of particular interest. Gp96 is a 96 kDa glycoprotein localized to the endoplasmic reticulum, which can also be found at the cell surface. Gp96 has been shown to be released into the extra cellular space during necrotic cell death and activates dendrite cells and macrophages by realizing inflammatory cytokines and inducing dendrites cells to mature. Extra-cellular gp96 has been known to activate dendrite and macrophages by modulating inflammatory cytokines and inducing maturation of dendrites.

Gp96 has the ability to transfer antigenic peptides for their MHC-class 1-restricted presentation and allows gp96 to function as an efficient messaging system alerting the immune system of an infection. This includes the receptor-mediated uptake of gp96 by dendrite cells. The receptor is CD91, which is known as the $\alpha 2$ macroglobulin ($\alpha 2M$) receptor expressed on phagocytes. The presentation of gp96-associated peptide by antigen-presenting cells ("APC's") is induced by $\alpha 2$ macroglobulin. Gp96 is bound by CD91 on dendrite cells and internalized. Gp96 induces the expression of co-stimulatory molecules and the release of interleukin 12 (IL-12) and tumor necrotic factor $\alpha$ ("TNF$\alpha$") by the APC.

Certain infections, such as by the human immunodeficiency virus, have also presented challenges in targeting the disease-causing organism and neutralizing it. Typically, infection with the human immunodeficiency virus, HIV-1, eventually causes acquired immunodeficiency syndrome (AIDS) and an associated syndrome, AIDS-related complex (ARC). Neutralizing this virus has proved difficult, largely because its structure obstructs immune system access to viral epitopes and its genetic material is highly variable. Accordingly, researchers have been seeking prophylactic and therapeutic methods for preventing or controlling HIV which are not dependent upon antibody-mediated immunity.

It has been recognized that denying entry into CD4+ cells to the HIV-1 virus could at least slow the progress of the infection and alleviate, if not cure, the disease and/or its symptoms. The complex mechanism by which the virus crosses the cell membrane has been widely investigated. Broadly, the entry of human immunodeficiency virus into, for example, CD4+ Th1 cells (T-helper type 1 cells), is dependent upon a sequential interaction of the gp120/gp41 subunits of the viral envelope glycoprotein gp160 with the CD4+Th1 cell surface glycoprotein and the cell surface receptor CCR5. The "env" gene of HIV encodes a single protein, gp160. Gp160 travels to the cell surface where cellular enzymes cleave it into gp120 and gp41. If and when new virus particues bud off from the host cell, these two pieces lie on opposite sides of the virus membrane. Gp120 sits on the outside of the virus particle, forming the virus' spikes, while gp41 sits just on the inside of the membrane, with each gp41 unit being anchored to a gp120 through the membrane. On binding of gp120 with its cell surface binding sites, a conformational change in the latent gp41 subunit through an intermediate state to an active state is initiated, inducing fusion of the viral and cellular membranes and transport of the virus into the cell (Weissenhom et al., *Nature*, 387:426-30 (1997)).

Numerous binding experiments have been conducted in an effort to find antiviral ligands that will effectively compete with the HIV-1 for CD4+ gp and/or CCR5 binding sites, or that will preferentially block gp120 and/or gp41 binding domains. The frequent mutability of the gp41 and gp120 surface antigens, however, lessens the chance that traditional approaches for creating immunity will be successful against HIV. Therefore, new approaches employing gp41 and gp120 complexes with new immunomodulators which increase their immunogenicity are needed.

BRIEF DESCRIPTION OF THE DRAWINGS

Some aspects of the present invention are generally shown by way of reference to the accompanying drawings in which:

FIG. 1 illustrates the porcine pepsinogen sequence, and major and minor sequences of this pepsinogen;

FIG. 10 shows amino acid normalization for the 45 kDa IPF fragment according to one embodiment of the invention;

FIG. 11 shows amino acid normalization data for an IPF fragment according to one embodiment of the present invention;

FIG. 12 shows amino acid normalization data for an IPF fragment according to one embodiment of the present invention;

FIG. 13 shows a chart summarizing binding of immobilized target molecules and soluble ligands, which include CD4, Gp41 (short) Gp120, Gp41 (long), human serum and IPF fragments according to one embodiment of the present invention;

SUMMARY OF THE DISCLOSURE

Figure 2:
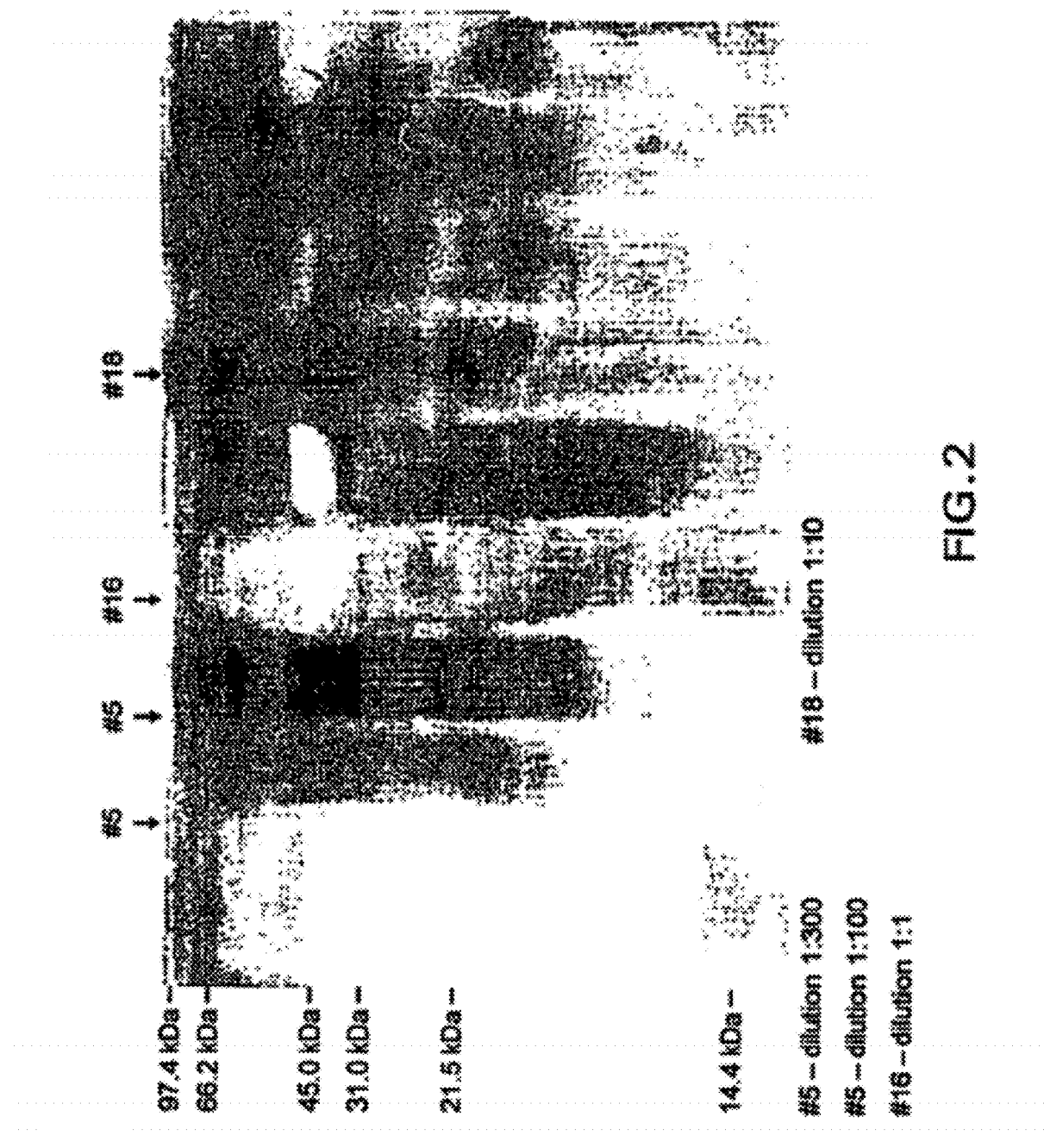
FIG. 2 is a photograph of an electrophoresis gel, showing an inactivated pepsinogen fragment ("IPF") in the 45.0 kDa band.

The present invention includes methods and compositions comprising modified cellular shock protein gp96 which preferably includes an irreversible pepsin fraction IPF and more preferably includes an IPF-gp96 complex. In another preferred embodiment, a complex of IPF-gp96 may be combined with at least one other polynucleotide like a molecular adjuvant, such as IL-2, to increase cellular immune response.

The present invention also encompasses a cancer preventive or therapeutic vaccine comprising an IPF-gp96 complex, and more specifically, complexes of IPF-1-gp96; IPF-2-gp96; IPF-3gp96, IPF-4-gp96, IPF-5-gp96, singly or in combinations thereof, which may be mixed with one or more polynucleotides encoding a molecular adjuvant. Any molecular adjuvant that increases cellular immune response may be used such as cytokine IL-2. In the preferred embodiments, the compositions and methods of the present invention comprise binding between IPF fragments and receptors of gp96, such as for example, CD91, in vivo. Administration may be via an intramuscular injection. The cancer to be treated may be primary or metastatic and the patients to be treated may have multiple different types of cancer. The anti-tumor IPF compositions disclosed herein may induce cytotoxic T-cell responses against tumor cells and may bind to at least one receptor restricted to antigen-presenting cells (APC's).

In one embodiment, certain IPF compositions disclosed herein, including IPF-6, have demonstrated increased synthesis of Th-1 cells and display significant affinity binding to gp41, thus preventing the HIV virus from fusing with CD4 cells and increasing the antigenic activity of gp41 and gp120, stimulating virus-specific CD8 cells that induce apoptosis in the CD4 cells. Apoptosis is a beneficial physiological mechanism in chronic viral diseases since it has been shown that inhibiting this process leads to increased viral replication.

The anti-tumor and anti-viral IPF compositions disclosed herein may mediate maturation of dendrite cells as determined by up-regulation of MHC class-II, CD86 and CD83 molecules, regulation of pro-inflammatory cytokines IL-12 and INF-$\chi$, increase synthesis of Th-1 cells and enhance the stimulatory capacity of T-cells. These include modulation of complement activation; saturation of Fc receptors on macrophages; and suppression of various inflammatory mediators, including cytokines and chemokines. The helper $T_1$ cells then elaborate cytokines INF-$\gamma$ and IL-2 that selectively promote the cell-mediated immune response.

Other embodiments of the present invention are generally directed to providing pharmaceutical compositions comprising IPF (IPF-1, IPF-2, IPF-3, IPF4, IPF-5 and/or IPF-6) and methods for preventing, treating, and diagnosing HIV-1 infections and HIV-1 related conditions such as AIDS (Acquired immune Deficiency Syndrome) and ARC (AIDS Related Complex) with these compositions.

In an exemplary embodiment the present invention relates to a method of modulating immune system activity comprising administering to a patient an effective amount of a composition containing inactivated pepsin fragment (IPF).

The isolation, purification and characterization and a variety of other uses, e.g., diagnosis and treatment of HIV infection and related diseases such as AIDS and ARC, of the inactivated pepsin fragment or fraction (IPF) as used herein is described in commonly owned U.S. Provisional Patent Application No. 60/644,054, filed Jan. 18, 2005, Zhabilov, the contents of which are incorporated herein by reference in their entirety.

According to Entrez Protein, accession number NP_999038. a sequence of swine porcine pepsinogen (SEQ ID NO: 7) is—

```
MKWLLLSSLV  VLSECLVKVP  LVRKKSLRQN  LIKNGKLKDF  LKTHKHNPAS  KYFPEAAALI   60

GDEPLENYLD  TEYFGTIGIG  TPAQDFTVIF  DTGSSNLWVP  SVYCSSLACS  DHNQFNPDDS  120

STFEATSQEL  SITYGTGSMT  GILGYDTVQV  GGISDTNQIF  GLSETEPGSF  LYYAPFDGIL  180

GLAYPSISAS  GATPVFDNLW  DQGLVSQDLF  SVYLSSNDDS  GSVVLLGGID  SSYYTGSLNW  240

VPVSVEGYWQ  ITLDSITMDG  ETIACSGGCQ  AIVDTGTSLL  TGPTSAIAIN  IQSDIGASEN  300

SDGEMVISCS  SIDSLPDIVF  TINGVQYPLS  PSAYILQDDD  SCTSGFEGMD  VPTSSGELWI  360

LGDVFIRQYY  TVFDRANNKV  GLAPVA                                          386
```

According to Kamatari et al., after the N-terminal 60 bases of pepsinogen are cleaved off to produce pepsin, the N-terminal lobe of pepsin protein includes residues 1-172, and the C-terminal lobe includes the remaining residues 173-326. IPF-6 according to the invention herein differs from pepsin. It includes a major component having an apparent MW of 45 kD when subjected to SDS-PAGE as shown in FIG. 2. It is unclear whether the 45 kD IPF-6 peptide is actually larger than pepsin, e.g. due to dimerization or other bonding with itself or another peptide, or whether the 45 kD apparent molecular weight is an artifact due to chemical modification of the protein such as methylation. The term "45 kD IPF-6" is used here to refer to the IPF-6 molecule obtained and assayed as described here, whether its actual molecular weight is 45 kD or another figure.

Surprisingly, preparations isolated from pepsin provide highly sensitive, specific, and therapeutic biological preparations. The starting material may be pure, active porcine pepsin A. An exemplary starting material may be Sigma porcine pepsin P 7000, which has a concentration of 1:10000. This is a pepsin A from porcine gastric mucosa, is a powder with 800-2,500 units/mg protein (CAS #9001-75-6, EC #3.4.23.1). Other starting material preparations are acceptable and may be effective according to the invention. For example, porcine pepsin with other concentrations may be used, e.g. 1:60000. Other natural or recombinant sources of pepsin may be used, or other similar aspartic proteases, provided that the protease is preferably inactive at alkaline, neutral, near-neutral, or mildly acidic pH, has a pI in those ranges, and has a sequence with substantial homology to the IPF 45kD fragment reported here. Substantial homology means at least about 50, 60, 70, 80, 90, or 95% identity of amino acid residues in the relevant portions of the molecule, or structural homology.

The invention provides several uses for the peptides. Examples of possible uses include a diagnostic assay and a therapeutic agent. IPF causes a dramatic rise in cytokines (e.g. interleukin 9 and 10) and antibodies to p24 antigen in HIV patients.

The properties of the peptides identified as part of the IPF herein include molecular weight, inactivity at neutral pH, as present in blood, and their partial sequence data. Also, the IPF fragments migrate as a single main peak in HPLC, such as shown in the chromatogram of FIG. 1 for IPF-6, with a particular retention time. Because pepsin is inactivated during isolation of IPF, the preparation is preferably stable and does not degrade significantly over time.

The inactivated pepsin fragments (IPF) of the invention may be referred to as irreversibly-inactivated. This is due to its treatment at neutral pH. As noted above, inactivation occurs above about pH 5, and becomes irreversible above about pH 6, and proteolytic activity is lost by such treatment. Maximal activity of pepsin as an enzyme is between 2-4 pH. The inventive method preferably increases the pH of diluted pepsin to above 5, above about 6, and desirably in the range of pH 6.6-6.8 before precipitation and during use. Thus IPF formulation pepsin fragments are irreversibly inactivated.

As used herein, the present invention may be directed to modulating immune system activity, which includes treating decreasing, increasing, attenuating or modulating any condition that may benefit from an enhancement of immune system activity. Immune conditions can include immune diseases or disorders. Immune disorders may include Allergies, Auto-Immune, DiGeorge Syndrome, Familial Mediterranean Fever, Immune Deficiency, and Multiple Chemical Sensitivity.

Immune system disease or disorder may include at least one of Agammaglobulinemia, Anaphylaxis, Antiphospholipid Syndrome, Ataxia Telangiectasia, Autoimmune Diseases, Common Variable Immunodeficiency, DiGeorge Syndrome, Electrosensitivity, Familial Mediterranean Fever, Graft vs Host Disease, Granulomatous Disease, Chronic, HIV Infections, Hypersensitivity, Hypersensitivity, Immediate, IgA Deficiency, Immune Complex Diseases, Immune System Diseases, Immunologic Deficiency Syndromes, Lambert-Eaton Myasthenic Syndrome, Lambert-Eaton Myasthenic Syndrome, Latex Hypersensitivity, Lymphoproliferative Disorders, Multiple Chemical Sensitivity, Purpura, Schoenlein-Henoch, Samter's Syndrome, Severe Combined Immunodeficiency, Sick Building Syndrome, Sjogren's Syndrome, and Wiskott-Aldrich Syndrome.

In accordance with one aspect of the present invention, auto-immune disorder may comprise Addison's, Ankylosing Spondylitis, Antiphospholipid Syndrome, Barth Syndrome, Graves' Disease, Hemolytic Anemia, IgA Nephropathy, Lupus Erythematosus, Systemic, Microscopic Polyangiitis, Multiple Sclerosis, Myasthenia Gravis, Myositis, Osteoporosis, Pemphigus, Psoriasis, Rheumatoid Arthritis, Sarcoidosis, Scleroderma and Sjogren's Syndrome. Examples of allergies may include Asthma, Food, Hay Fever—Rhinitis, Hives, Latex and Sinusitis. In yet another embodiment, the patient may have AIDS or AIDS Related Complex, multiple sclerosis, hepatitis, herpes, rheumatoid arthritis, autoimmune diabetes, encephaloniyelitis or another autoimmune disease.

In another exemplary embodiment, the present invention may encompass a cancer preventive or therapeutic vaccine.

In one exemplary embodiment, the composition further comprises an antigen and an adjuvant, which potentiates the immune response to the antigen. The adjuvant may be an aluminum-containing compound, e.g., aluminum hydroxide (AH) or aluminum phosphate (AP) labeled with $^{26}$Al. The AH adjuvant may be crystalline aluminum oxyhydroxide, AlOOH, and the AP adjuvant may be amorphous aluminum hydroxyphosphate. The adjuvant may be administered in an amount of preferably no more than about 0.85 mg aluminum per dose. In another exemplary embodiment, the adjuvants are substances that when mixed with antigens enhance the antibody response to the antigen itself. Additional molecular adjuvants may include various cytokines from interleukin types and adjuvant emulsion MF59 which is approved for clinical use, or mineral oil which increases antigen persistence and recruits macrophages to the site of injection.

In yet another exemplary embodiment, the IPF may be administered with at least one other polynucleotide, like a molecular adjuvant, for cancer preventive or therapeutic vaccine. The cancer may be either primary or metastatic and may include renal cell carcinoma (kidney cancer), melanoma, pancreatic cancer, non-Hodgkin's lymphoma, lung carcinoma, prostate cancer, spinal cell carcinoma, soft tissue sarcoma or fibrosarcoma.

In an exemplary embodiment, the molecular adjuvant may be interleukin 2 (IL-2). The IL-2 may be used to increase cellular immune response to activate normal human lymphocytes by directly promoting cellular functions selected from the group comprising of IL-2 stimulated T-cells, which exhibit enhanced cytotoxicity and produce lymphokins, e.g., INF-$\gamma$ TNF-$\beta$ and TGF-$\beta$; B-cells growth factors, e.g., IL4 and IL-6 and GM-CSF. IL-2 may also induce lymphokine-activated killer (LAK) activity which is predominantly due to NK cells or increase production of T-cell clones.

The IPF compositions and complexes disclosed herein may be administered in a variety of manners, e.g., orally, intradermally, intramuscularly, subcutaneously or intravenously, or by intranasal spray. It may be in the form of an injectable solution or formulation, tablet, liquid formulation, lyophilized or aerosolized receptors. In one embodiment, the complex is administered intramuscularly. Also, doses may be administered at least daily, weekly or monthly, for as long as treatment is required. In exemplary embodiments, the complex may be administered intramuscularly once a week for four weeks, once a week for six weeks, three times a week for six weeks, or three times a week for 3 weeks.

Dosing duration may vary based on a variety of factors, e.g., if used as a therapeutic or preventive vaccine. For example, dosing may vary for a 2 ml vial of HSP-IPF complex composition containing 12 mg of IPF and 2.77 µg of gp96. In an exemplary embodiment, the complex may be used as a therapeutic vaccine and a total of 18 vials are administered three vials a week for 6 weeks. After three months, a total of nine vials may be administered once a week for 9 weeks. In another exemplary embodiment, the complex may be used as preventive vaccine and a total of 10 vials may be administered three vials a week for 3 weeks.

The HSP may be administered via the complex in a variety of doses, e.g., from about 1.0 to about 200 µg. As used herein low doses of HSP may be from about 1.0 to about 25 µg and high doses of HSP may be from about 26 to about 200 µg. In accordance with one aspect of the present invention, a low dose may be about 1.0, 10 or about 25 µg, and a high dose may be about 26, 48, 50, 75, 100, 150 or 200 µg. The amount designation of low or high doses may vary based on the frequency of administration. For example, an amount of about 25 µg may be deemed high if administered more frequently or may be deemed low if administered less frequently.

The IPF may be administered via the complex in a variety of doses, e.g., from about 1 to about 25 mg of per 1 ml of the composition. In accordance with one exemplary embodiment of the present invention, the IPF may be administered in about 2 mg/ml, about 4 mg/ml, about 6 mg/ml, about 8 mg/ml, about 10 mg/ml or about 12 mg/ml.

In accordance with another embodiment of the present invention, the IPF-HSP complex may be administered as pharmaceutical composition comprising about 10 µg/ml HSP, about 6 mg/ml IPF, and optionally including about 0.016 M Aluminum Phosphate (about 2.26 mg/ml AlPO$_4$) (or about 0.5 mg/ml Al$^{3+}$), about 0.14 M NaCl, about 0.004 M CH$_3$COONa, and about 0.004 M KCl.

In accordance with yet another embodiment of the present invention, the IPF-HSP complex may be administered as pharmaceutical composition comprising about 100 µg/ml HSP, about 4 mg/ml IPF, and optionally including about 0.016 M Aluminum Phosphate (about 2.26 mg/ml AlPO$_4$) (or about 0.5 mg/ml Al$^{3+}$), about 0.14 M NaCl, about 0.004 M CH$_3$COONa, and about 0.004 M KCl.

In an alternative aspect, the formulation may include about 10 µg/ml HSP, about 4 mg/ml IPF, about 2.26 mg/ml Aluminum Phosphate, about 0.5 mg/ml Aluminum, about 12.9 mg/ml sodium citrate and about 4.1 mg/ml sodium acetate. In accordance with one embodiment of the present invention, the formulation may include about 100 µg/ml HSP, about 4 mg/ml IPF, about 2.26 mg/ml Aluminum Phosphate, about 0.5 mg/ml Aluminum, about 12.9 mg/ml sodium citrate and about 4.1 mg/ml sodium acetate.

In accordance with yet a further embodiment of the present invention, the formulation may comprise per vial, about 10 µg HSP (e.g. gp96), about 8 mg IPF, about 4.52 mg Aluminum Phosphate, about 1.0 mg Aluminum, about 25.8 mg sodium citrate and about 8.2 mg sodium acetate. In another embodiment, the formulation may comprise per vial, about 100 µg HSP, about 8 mg IPF, about 4.52 mg Aluminum Phosphate, about 1.0 mg Aluminum, about 25.8 mg sodium citrate and about 8.2 mg sodium acetate.

In accordance with another exemplary embodiment of the present invention, the HSP component may be gp96, e.g., Glycoprotein-96 (MW 94 kDa). The gp96 may be purified from mouse cells, in an amount of about 1 mg/ml and having about 95% purity as determined by SDS-PAGE. In another aspect the IPF-gp96 complex may be a liquid suspension containing gp96 purified native protein and IPF purified protein fragment.

These formulations may further include IL-2, in an amount from about 1000000 to about 3000000 IU per vial.

In accordance with one aspect of the present invention, the formulation may contain low dose concentrations, e.g., 10 or 25 µg, of HSP (e.g. gp96) effective to induce pro-inflammatory responses, e.g., recognition of non-self-heat shock proteins leads to inflammatory responses. This may be useful to treat cancer and infectious diseases. Examples of a HSP component that may be used at low dose concentrations include Hsp70, Hsp90, gp96, calreticulin, Hsp110, grp170, covalent Hsp-antigen complexes or non-self-Hsp60.

In accordance with yet another aspect of the present invention, the formulation may contain high dose concentrations, e.g., 100 µg, of HSP (e.g. gp96) effective to induce regulatory immunity, e.g., recognition of conserved epitopes induces regulatory responses. Examples of a HSP component that may be used at high dose concentrations include gp96, self-Hsp60 or self-HSp70.

Combining HSP (e.g. gp96) and IPF (e.g. IPF-1, IPF-2, IPF-3, IPF-4 and/or IPF-5) in a complex contributes to a variety of synergistic effects. In one exemplary embodiment, the HSP may mediate one or more of the following effects: suppressing tumor immunity or eliciting protective immunity against tumor cells, chaperoning immune enhancing agents and peptides, activating dendrites and macrophages by modulating inflammatory cytokines and inducing maturation of dendrites, modulating release of IL-12 and tumor necrosis factor $\alpha$ (TNF$\alpha$), inducing anti-tumor activity and tumor-specific cytolytic T-cells and inducing cancer-specific CD8$^+$ T-cell response. In another exemplary embodiment, the IPF component may mediate one or more of the following phenotypic effects: increasing the CD4+CD45 RO+CD62 L population, increasing in CD4+CD45 RA+CD62 L population, inducing a second CD4+population having lower CD4 intensity but no increase in SSC, inducing a parallel increase in absolute CD4 cell counts, and increasing the CD8+CCR5+ population.

In accordance with yet another aspect of the present invention, the IPF component may mediate one or more of the following functional effects over time: increasing the IFN-γ containing CD3+CD4+ cells post stimulation in vitro, decreasing the IL-4 containing CD3+CD4+cells post stimulation, and increasing the IFN-γ containing CD3+CD8+cells over time.

In an exemplary embodiment, IPF peptides, e.g. IPF1-6, show specific binding and indicate usefulness as a) a diagnostic and b) a therapeutic for HIV, and other diseases. For example, preliminary trials have shown that the IPF (e.g. IPF-6), gp41 and gp120 bind together through-alpha-1,-alpha-2 and -beta serum fractions, which formed inside the body blocks direct HIV-CD4 contact and at the same time, triggers an immune reaction. The next antigen complex triggers an immune reaction model with the participation of T-lymphocytes with -gamma -delta chains on their surface.

Diagnostic methods using IPF fragments disclosed herein may be performed by combining IPF with test and control sera and conducting 2-D electrophoresis in 1% agarose gels, following the techniques set forth in Zhabilov et al. (US Patent Publication US 2004/0018639, filed Jan. 3, 2003 by Zhabilov, Harry P. et al., the content of which is incorporated herein in its entirety by reference), with modifications apparent to a person of ordinary skill. Therapeutic methods using IPF disclosed herein are performed by administering IPF pharmaceutical compositions to a subject having a disease susceptible to treatment with IPF. The formulations, dosages, dosing regimen, and routes of administering may be those described in Zhabilov et al. or other examples apparent to a person of ordinary skill in the art.

In another exemplary embodiment, the IPF compositions disclosed herein (e.g. IPF-1, IPF-2, IPF-3, IPF-4, IPF-5 and/or IPF-6) may be in a variety of forms, e.g., a pharmaceutical composition. In one aspect, the pharmaceutical compositions may comprise the IPF fragments and compositions disclosed herein and a pharmaceutically effective carrier, e.g., buffered saline, water, aluminum hydroxide, or another suitable adjuvant. The compositions disclosed herein may also contain preservatives, vehicles, buffers, tonicity adjusters, chelating agents, antioxidants and or other material. Examples of preservatives include Phenylethyl alcohol USP, Sorbic Acid NF, Sodium Propionate, Sodium Benzoate NF, and Benzyl alcohol NF. Examples of Vehicles include Purified Water USP, Hydroxy Ethyl Cellulose NF, Polyethylene Glycol NF, Povidone USP, Hydroxypropyl Methylcellulose F4M USP, Dextran 70 USP, Poloxamer NF, Polyoxyl-40-Stearate USP and Aluminum Chloride. Examples of buffers include Sodium Phosphate (mono, di and tribasic), Sodium Carbonate, Sodium Biphosphate, Sodium Bicarbonate USP, Citric Acid Monohydrate USP, Acetic Acid, Sodium Citrate USP, Phosphoric Acid, Glacial Acetic Acid USP, Sodium Hydroxide NF, Sodium Acetate USP, Potassium Citrate USP, Hydrochloric Acid NF, and Potassium Phosphates: (mono, di and tribasic). Examples of tonicity adjusters include Sodium Chloride USP, Dextrose USP, Glycerin USP, Potassium Chloride USP and Mannitol USP. Examples of chelating agents include Edetate Disodium USP, Edetate Monosodium, Edetic Acid NF, and Edetate Trisodium. Examples of antioxidants include Sodium Metabisulfite NF, Sodium Bisulfite, Sodium Thiosulfate USP, and Acetylcysteine USP. Other material may include Polysorbates (20-85) NF, Pluronic F168, Pluronic F127, and Polyethylene Glycol 300, 400, 6000 NF.

In one embodiment, the IPF compositions disclosed herein (e.g. IPF-1, IPF-2, IPF-3, IPF-4, IPF-5 and/or IPF-6) are administered intramuscularly. Also, doses may be administered at least daily, weekly or monthly, for as long as treatment is required. In exemplary embodiments, the IPF is administered intramuscularly once a week for six weeks, twice weekly for eight weeks, or as sixteen injections with two injections on consecutive days per week for eight weeks.

The IPF disclosed herein (e.g. IPF-1, IPF-2, IPF-3, IPF4, IPF-5 and/or IPF-6) may be administered via the composition in a variety of doses, e.g., from about 1 to about 25 mg of per 1 ml of the composition. In an exemplary embodiment, the IPF is administered in about 8 mg or about 4 mg per 2 ml of formulation. The IPF may be administered in an amount of 57 μg per 1 kg of body weight of the patient. In mice, e.g., IPF may be administered from about 0.1 to about 0.5 mg/kg of body weight and in rabbits, about 1.24 mg/kg, twice weekly for eight weeks.

The IPF disclosed herein (e.g. IPF-1, IPF-2, IPF-3, IPF4, IPF-5 and/or IPF-6) may have one or more of the following effects: suppressing tumor immunity or eliciting protective immunity against tumor cells, chaperoning immune enhancing agents and peptides, activating dendrites and macrophages by modulating inflammatory cytokines and inducing maturation of dendrites, modulating release of IL-12 and tumor necrosis factor α (TNFα), inducing anti-tumor activity and tumor-specific cytolytic T-cells and inducing cancer-specific CD8$^+$ T-cell response.

The IPF components disclosed herein (e.g. IPF-1, IPF-2, IPF-3, IPF-4, IPF-5 and/or IPF-6) may have one or more of the following phenotypic effects: increasing the CD4+CD45 RO+CD62 L population, increasing in CD4+CD45 RA+CD62 L population, inducing, a second CD4+population having lower CD4 intensity but no increase in SSC, inducing a parallel increase in absolute CD4 cell counts when this phenomenon appears, and increasing the CD8+CCR5+ population.

The IPF component (e.g. IPF-1, IPF-2, IPF-3, IPF-4, IPF-5 and/or IPF-6) may have one or more of the following functional effects over time: increasing the IFN-γ containing CD3+CD4+cells post stimulation in vitro, decreasing the IL-4 containing CD3+CD4+cells post stimulation, and increasing the IFN-γ containing CD3+CD8+cells over time.

DETAILED DESCRIPTION OF THE INVENTION

Certain embodiments of the present invention are generally directed to providing isolated peptides characterized by, respectively, the amino acid sequences TLTSGGGAIALPPSMAAPPLGPVAPLTGAIHAPTXG (SEQ ID: NO 1), a fragment of approximately 45 kDa; TLSTATGGAIPPVAAMP-PGLVAPTHGPAIHP (SEQ ID: NO 2); NXVPVSVEGYXQITLDSITX (SEQ ID: NO. 3), a fragment of approximately 13.5 kDa; MTLTTGSGAIAPAMPPGLP-PHTGAIHAPM (SEQ. ID: NO. 4); and CCATSGPC-GAVMILTPHLTA (SEQ. ID: NO. 5), and a significant in vitro binding affinity for gp96. The peptides, referred to herein as, respectively, IPF-1, IPF-2, IPF-3, IPF-4 and IPF-5 (Inactivated Pepsinogen Fragments-1-5), were isolated from porcine pepsinogen, purified, and irreversibly inactivated for use in cancer therapeutic procedures.

The present invention also encompasses a cancer preventive or therapeutic vaccine comprising IPFgp96, and more specifically IPF-1-gp96; IPF-2-gp96; IPF-3-gp96, IPF-4-gp96 and IPF-5-gp96 or combinations thereof, which may be mixed with one or more polynucleotides encoding a molecular adjuvant. Any molecular adjuvant that increases cellular immune response may be used like cytokine IL-2. The cancer to be treated may be primary or metastatic and the patients to be treated may have multiple different types of cancer.

The heat shock protein, e.g., gp96, may be prepared according to suitable methods known in the art, such as according to the methods set forth in Chandawarkar, et al. (*Int'l Immunology*, "Immune modulation with high-dose heat shock protein gp96: therapy of murine autoimmune diabetes and encephalomyelitis," Vol. 16, No. 4, 615-624 (2004)), incorporated in its entirety by this reference. Complexes comprising HSP and IPF may be prepared according to suitable methods known in the art, such as disclosed in application No. PCT/US2006/038045, also incorporated in its entirety by this reference. In an exemplary embodiment, the HSP may comprise a modified cellular shock protein purified from either cancer or normal cell tissue. The tissue used may be that of the patient.

As used herein, heat-shock proteins may be referred to as HSPs or stress proteins, and may be used as molecular chaperones for protein molecules. They may be cytoplasmic proteins and can perform functions in various intra-cellular processes. The HSPs can also be referred to according to their molecular weights, for example Hsp70 and Hsp90, each of which define families of chaperones. The major classes of heat shock proteins are tabulated below. Although some members of each family are listed here, it should be noted that some species may express additional chaperones, co-chaperones, and heat shock proteins not listed. Additionally, many of these proteins may have multiple splice variants (Hsp90α and Hsp90β, for instance) or conflicts of nomenclature (Hsp72 is sometimes called Hsp70). Examples include heat shock proteins having an approximate molecular weight (kDa) of 10 kDa, e.g., Hsp10, 20-30 kDa, e.g., Hsp27, 40 kDa, e.g., Hsp40, 60 kDa, e.g., Hsp60, 70 kDa, e.g., Hsp70, Hsc70, Hsp72, Grp78 and BiP, 90 kDa, e.g., Hsp90 and Grp94, and 100 kDa, e.g., Hsp104, Hsp110.

The present invention also relates to a method of preparing HSP-IPF complexes (e.g. gp96 and IPF-1 through IPF-5). The HSP-IPF complex may be prepared in a variety of manners. In an exemplary embodiment, the HSP-IPF complex is prepared by spontaneous binding, e.g., covalently bonded. The isolated IPF and the isolated HSP may be diluted in a buffer solution and an adjuvant may be added. In accordance with one aspect of the present invention, the solution is maintained at a temperature of about +4 Celsius and incubated for a period of 12 hours. In one aspect, further chemicals, e.g., stabilizers, may be added.

In an exemplary embodiment, the IPF (e.g. IPF-1, IPF-2, IPF-3, IPF4, and/or IPF-5) is isolated from lyophilized pepsin and the HSP component used is gp96, readily lyophilized (P14625-human tumor rejection antigen-gp96). The IPF and gp96 are diluted in a buffer solution and after an incubation period of 12 hours aluminum phosphate is added as an adjuvant at a temperature of about +4 Celsius. In another aspect, further stabilizer may be added, e.g, sodium caprylate or sodium acetyltryptophanata.

In one aspect, the complex is prepared, by adding 12 milligrams (mg) of IPF (6 mg per ml) and 5.5 micrograms (μg) of gp96 (2.75 micrograms per ml) per 2 ml vial (or for a human dose, e.g., of about 100 micrograms per treatment, four times at weekly intervals. Adjuvant such as aluminum phosphate is added in an amount of about 0.004 M. In another aspect, about 0.004M Sodium Caprylate or 0.004 M Sodium Acetyltryptophanate may be added to stabilize the solution.

In another exemplary embodiment, the IPF-HSP complex (e.g. gp 96 and IPF-1, IPF-2, IPF-3, IPF-4 and/or IPF-5) may be in a variety of forms, e.g., a pharmaceutical composition. In one aspect, the pharmaceutical composition may comprise the IPF-HSP complex and a pharmaceutically effective carrier, e.g., buffered saline, water, aluminum hydroxide, or another suitable adjuvant.

Figure 9:
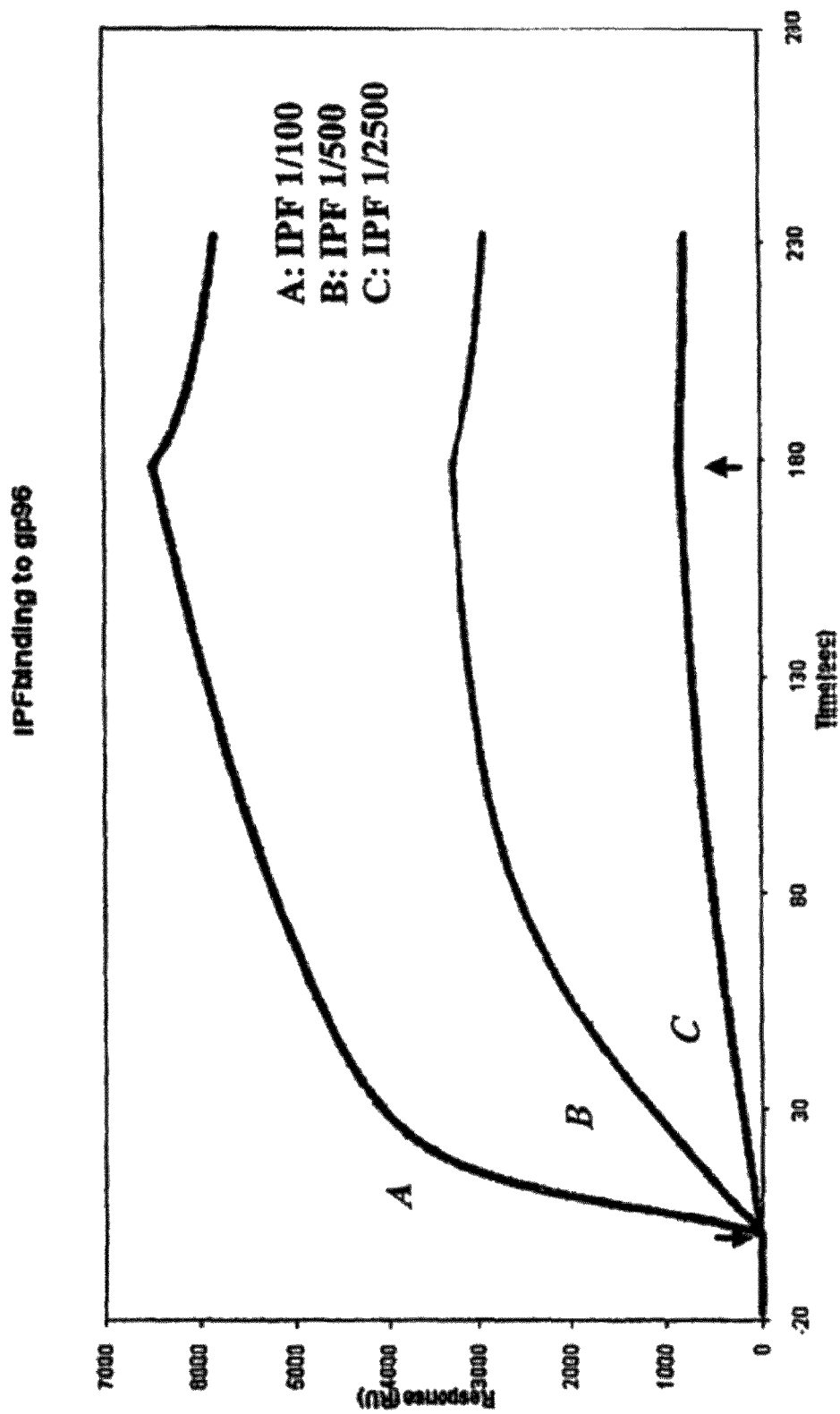
FIG. 9 is a graph showing binding of an IPF with heat shock protein gp96 at dilutions of IPF 1/2500, IPF 1/500 and IPF 1/100, according to one embodiment of the invention.
Figure 14:
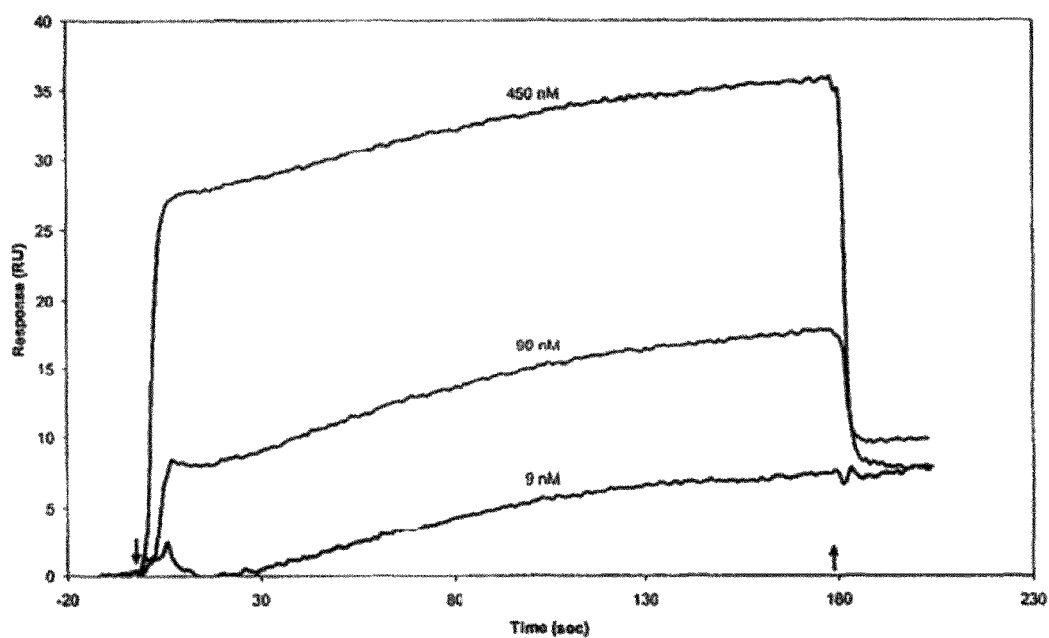
FIG. 14 shows a graph of binding of CD4 with immobilized IPF according to one embodiment of the present invention.
Figure 15:
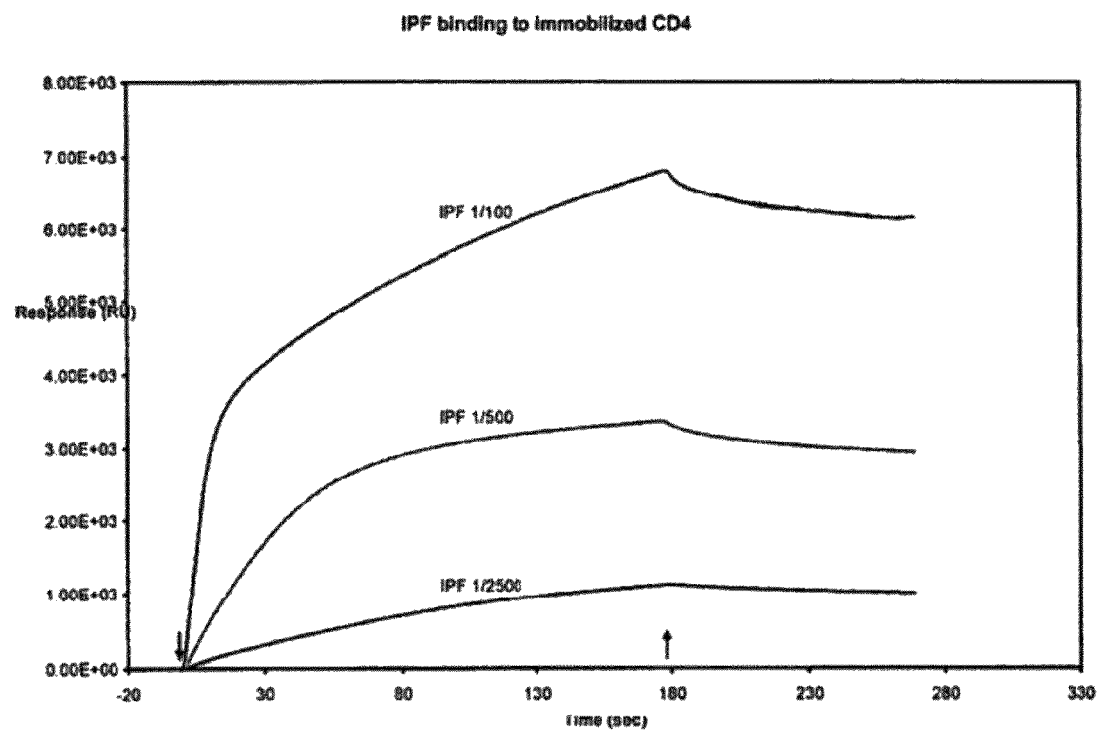
FIG. 15 shows a graph of binding of IFP binding with immobilized CD4 at IPF dilutions of 1/100, 1/500 and 1/2500 according to one embodiment of the present invention.
Figure 16:
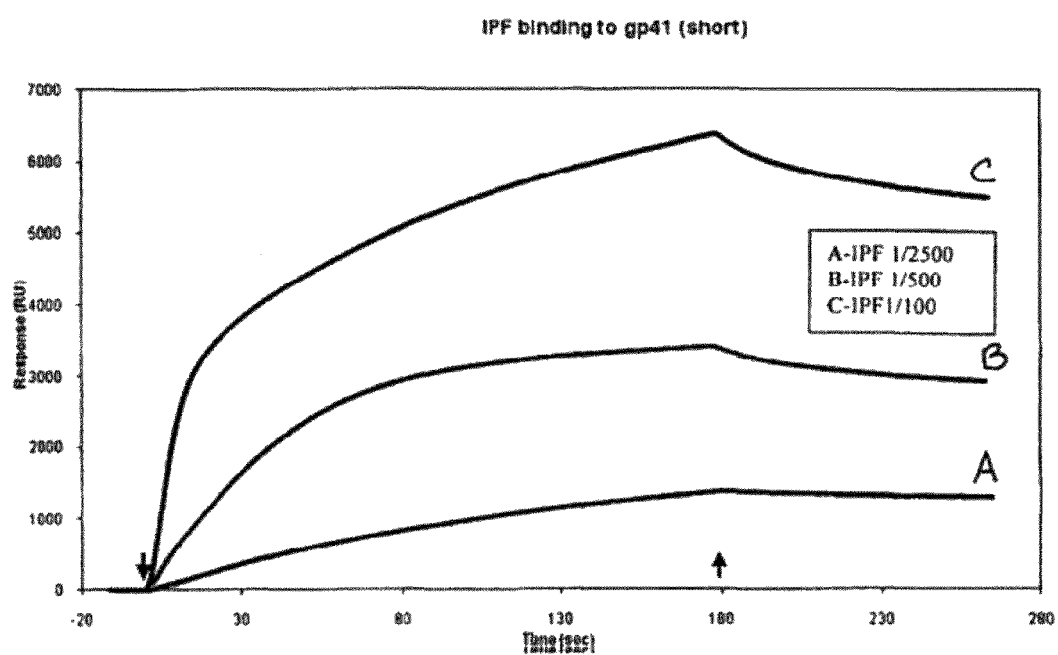
FIG. 16 shows a graph of binding of IPF to gp41 (short) at IPF dilutions of 1/2500, 1/500 and 1/100 according to one embodiment of the present invention.
Figure 17:
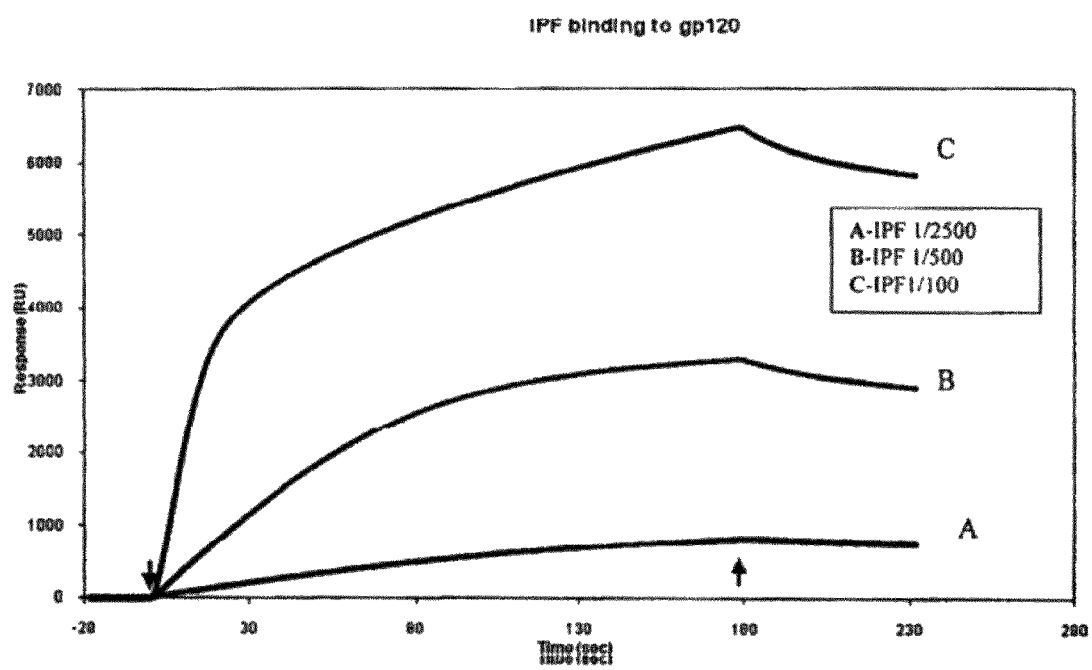
FIG. 17 shows a graph of binding of IPF with immobilized gp120 at IPF dilutions of 1/2500, 1/500 and 1/100 according to one embodiment of the present invention.
Figure 18:
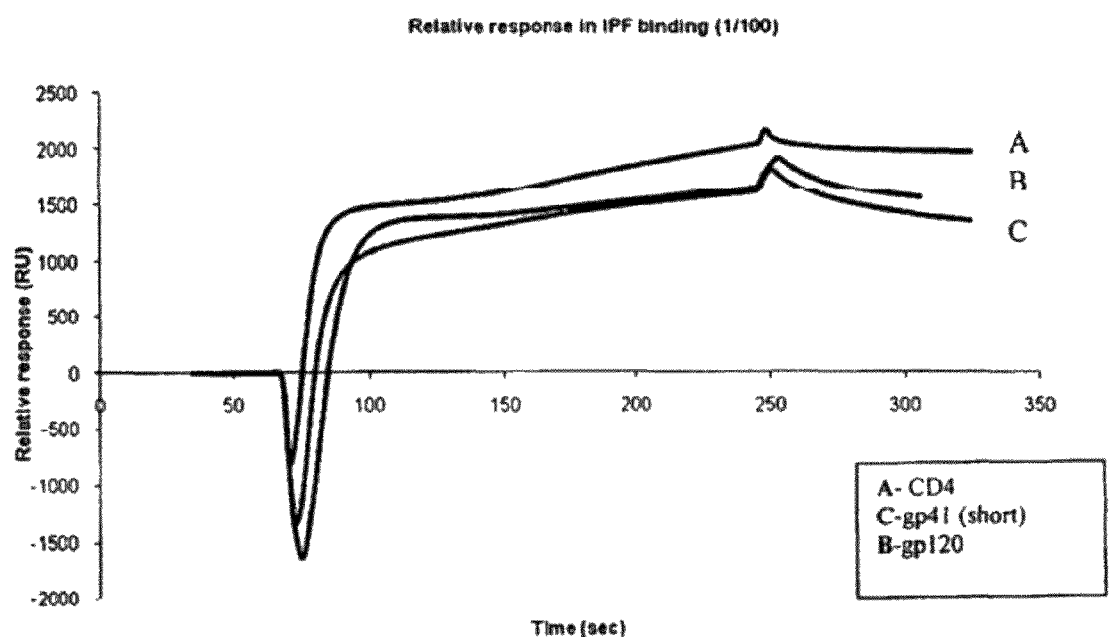
FIG. 18 shows a graph of relative response in IPF binding to CD4, gp41 (short) and gp120 at an IPF dilution of 1/100 according to one embodiment of the present invention.
Figure 19:
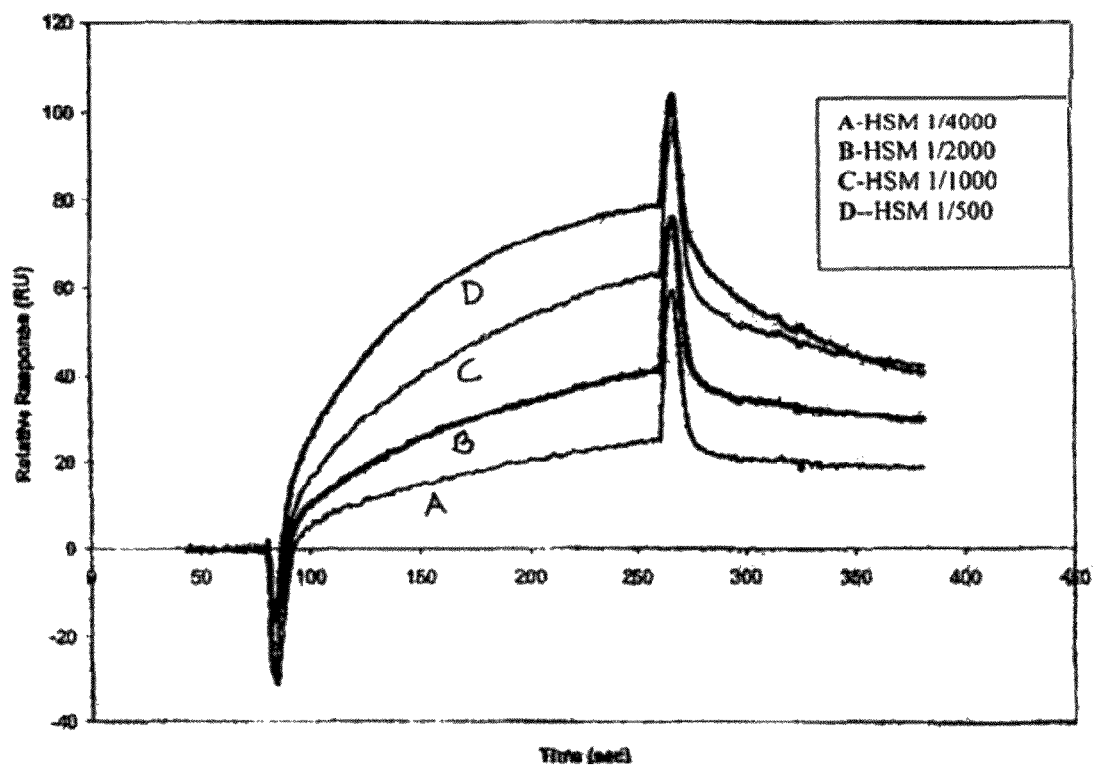
FIG. 19 shows a graph of human serum binding to immobilized IPF at human serum dilutions of 1/4000, 1/2000, 1/1000 and 1/500 according to one embodiment of the present invention.
Figure 20:
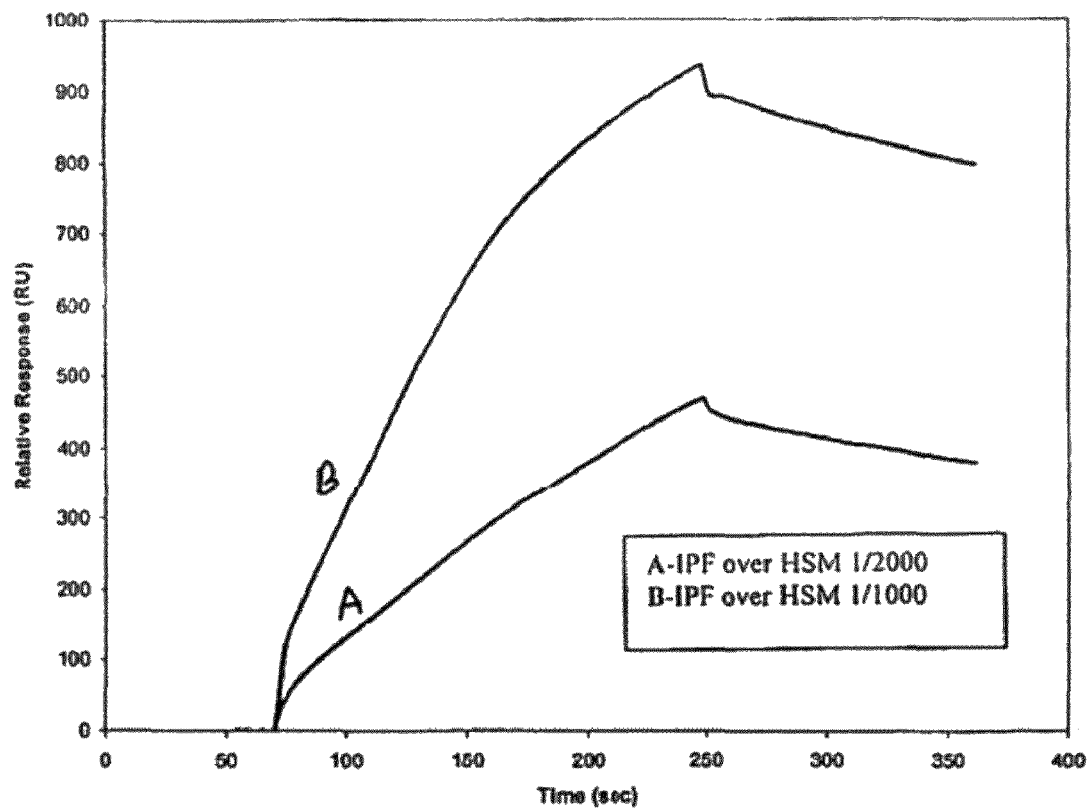
FIG. 20 shows a graph of IPF binding to immobilized human serum at IPF over human serum dilutions of 1/2000 and 1/1000 according to one embodiment of the present invention.
Figure 21:
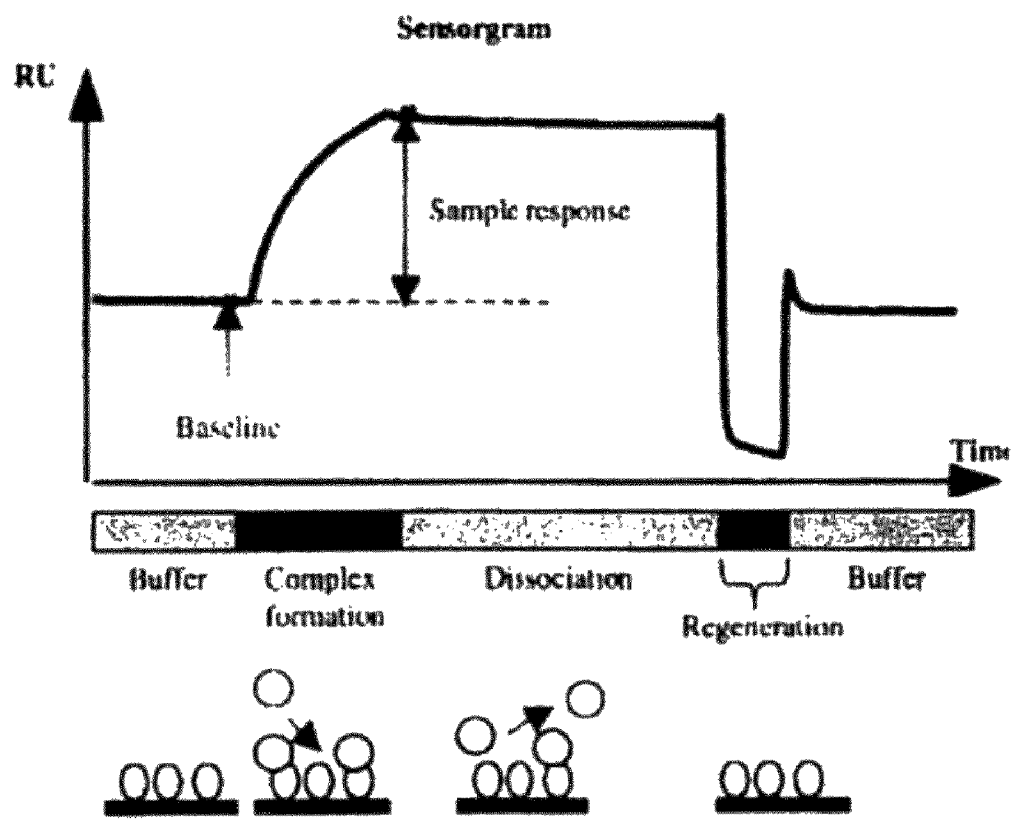
FIG. 21 shows a schematic representation of binding of IPF to human CD4 molecules. Initially buffer flows over the sensor surface coated with human CD4 molecules and a baseline is established. Analyte (IPF) is injected into the microreaction chamber and the signal is related to the binding of IPF to CD4 molecules. After injection, bound analyte (IPF) dissociates in the buffer flow. A regeneration solution is injected to dissociate remaining analyte (IPF) from the CD4 coated chamber.

FIG. 9 is a graph showing binding of an IPF with heat shock protein gp96 at dilutions of IPF 1/2500, IPF 1/500 and IPF 1/100, according to one embodiment of the present invention. A number of approaches may be used to detect complexing between IPF and gp96. By way of example, one such approach may be to obtain specific antibodies against IPF and gp96 and to build a sandwich immunoassay by suitable methods known in the art to detect the presence of these protein complexes. To detect binding of gp96 to IPF, the antigen may be coated on a plate to capture proteins from the sample and then report the binding with a specific detection antibody. The secondary (or detection) antibody may be directly labeled with MSD SULFO-TAG NHS ester or a SULFO-TAG-labeled anti-species, e.g., anti-mouse if the detection antibody is raised in mouse and the detection antibody is raised in a different species than the capture or primary antibody. Antibodies specific to IPF-gp96 complexes may also be used.

The cancer preventive vaccine may comprise a clear liquid opalescent suspension of spontaneous precipitate IPF (e.g., IPF-1, IPF-2, IPF-3, IPF4 and/or IPF-5) and gp96 molecules with IL2 as adjuvant and may comprise complexes of IPF-1, IPF-2, IPF-3, IPF4 and IPF-5 and gp96. Activity is preferably 1:0.6 measured by the ability of IPF to bind with gp96 (e.g., three molecules of IPF bound two molecules of gp96). The cancer preventive vaccine may be injected intramuscularly one injection per week for six weeks. The immune response probably gives evidence of two actions: 1) cytotoxic effect against tumor cells (cytotoxic T lymphocytes (CTLs) are effectors of CD8+ that can mediate the lysis of target cells bearing antigenic peptides associated with a MHC molecule. Other cytotoxic cells include gamma/delta chain and CD4+ NK 1.1+ cells); and 2) increased antibody production.

Other embodiments of the present invention are generally directed to providing an isolated antiviral peptide characterized by the amino acid sequence GDEPLENYLDTEYF (SEQ ID:NO 6) (-Gly-Asp-Glu-Pro-Leu-Glu-Asn-Tyr-Leu-Asp-Thr-Glu-Tyr-Phe-) ("IPF-6") and a significant in vitro binding affinity for HIV-1 gp120, gp 41 and human CD4 cells. The peptide has anti-retroviral activity in vivo, particularly anti-HIV-1 activity. The peptide, referred to herein as IPF-6 (Inactivated Pepsinogen Fragment-6), was isolated from porcine pepsinogen, purified, and irreversibly inactivated for use in HIV-1 prophylactic, therapeutic and diagnostic procedures. IPF-6 is expected to have anti-retroviral activity in vivo, particularly inhibition of HIV-1 entry into human CD4+ cells.

The exemplified peptide was obtained from porcine pepsinogen (FIG. 1) by isolation from a 45 kDa band of IPF preparation under gel electrophoresis (FIG. 2). It may also be derived from pepsinogen from any other source containing this sequence, or from any other peptides or proteins containing this sequence whereby suitable source pepsinogens are readily available commercially. Common laboratory methods and reagents for selectively cleaving intact proteins and for isolating and sequencing the cleaved peptides, such as the Erdman degradation process, may be used. The peptide may also be produced by peptide synthesis, using conventional methods. Moreover, genetically engineered constructs expressing the sequence of interest are generally preferred, although chemical syntheses may also be used.

Figure 3:
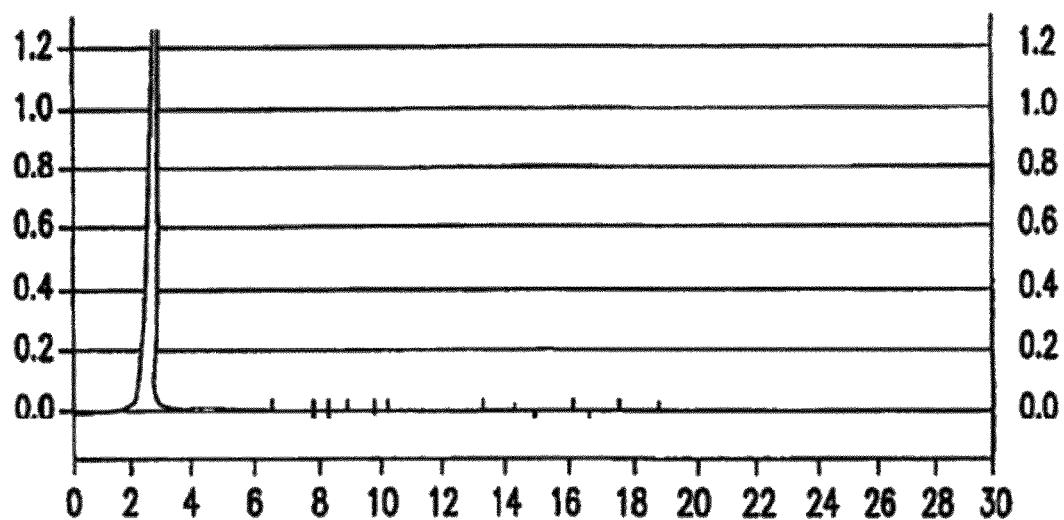
FIG. 3 is a Biacore graph showing a HPLC (High Performance Liquid Chromatography) chromatogram of an isolated IPF in accordance with once aspect of the present invention.
Figure 4:
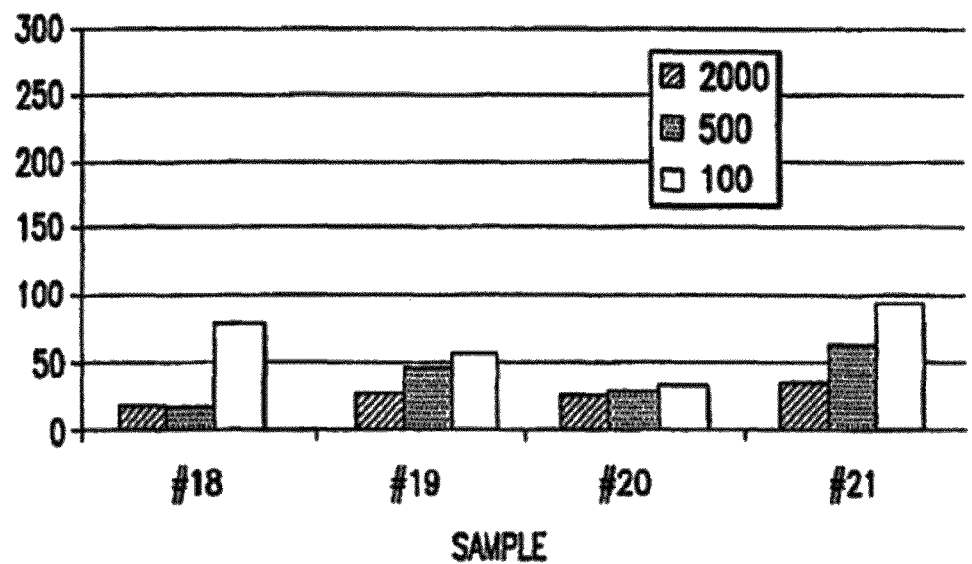
FIGS. 4, 5, 6, and 7 illustrate exemplary binding of four samples of IPF with gp41, gp120, human CD4, and human serum at 3 different dilutions.
Figure 5:
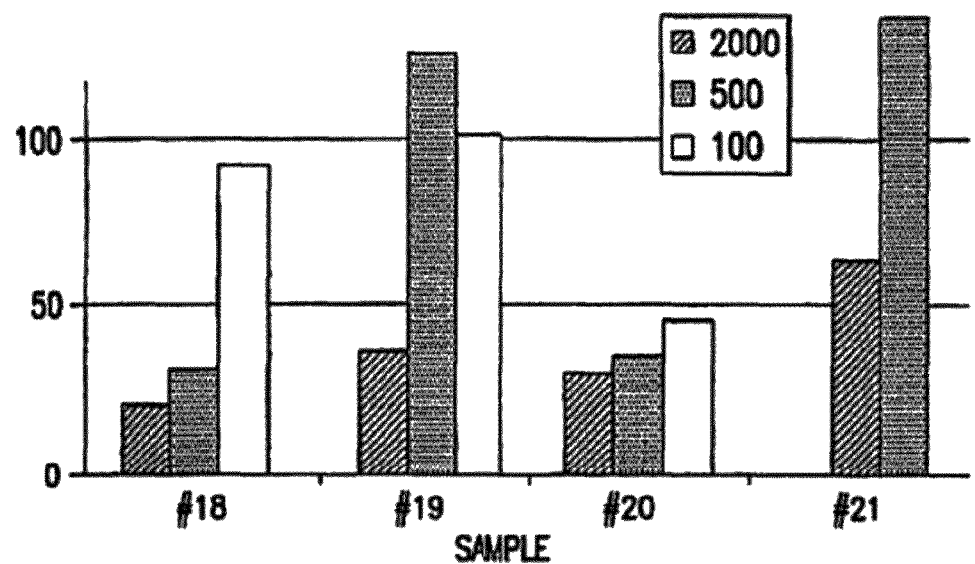
Figure 6:
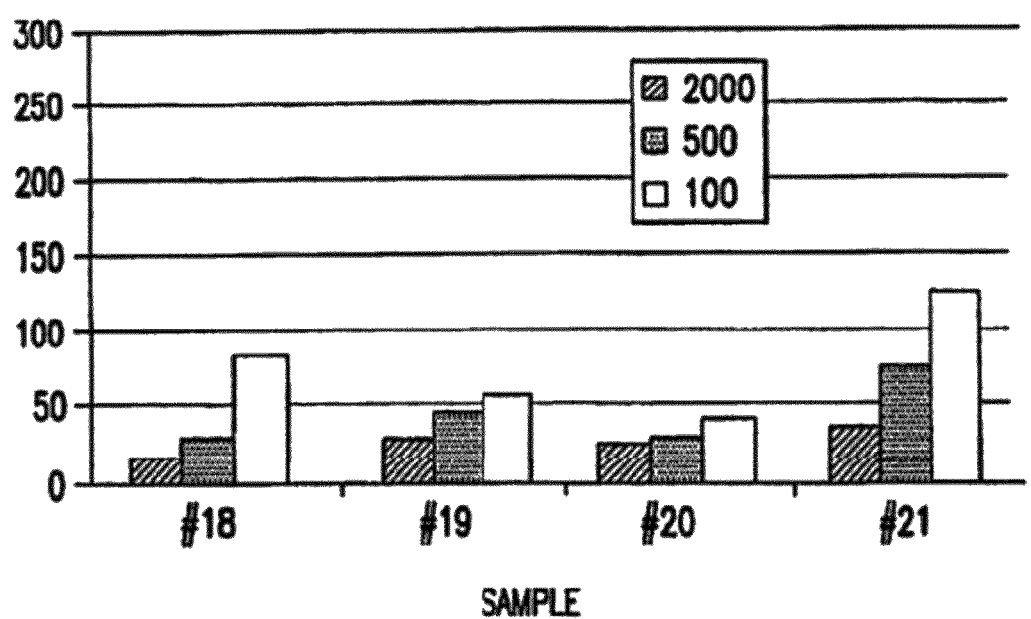
Figure 7:
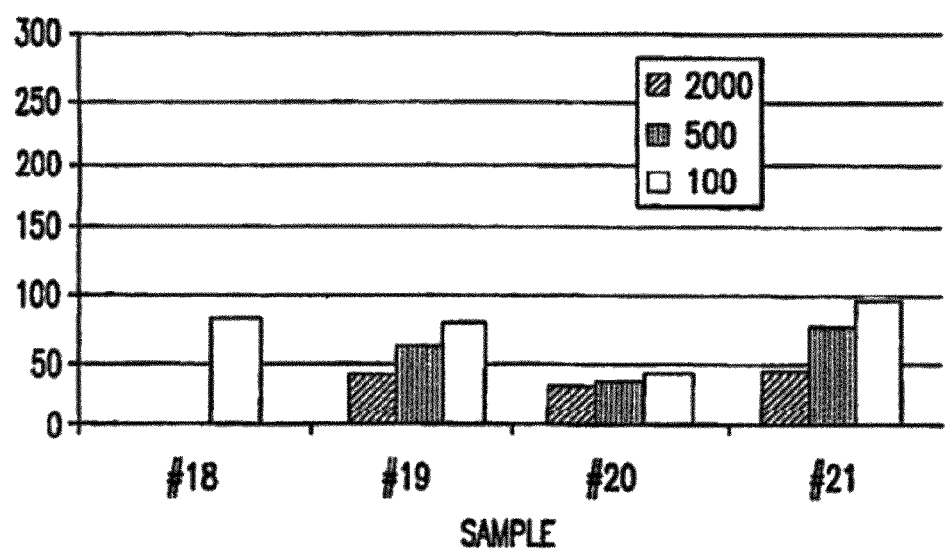
Figure 8:
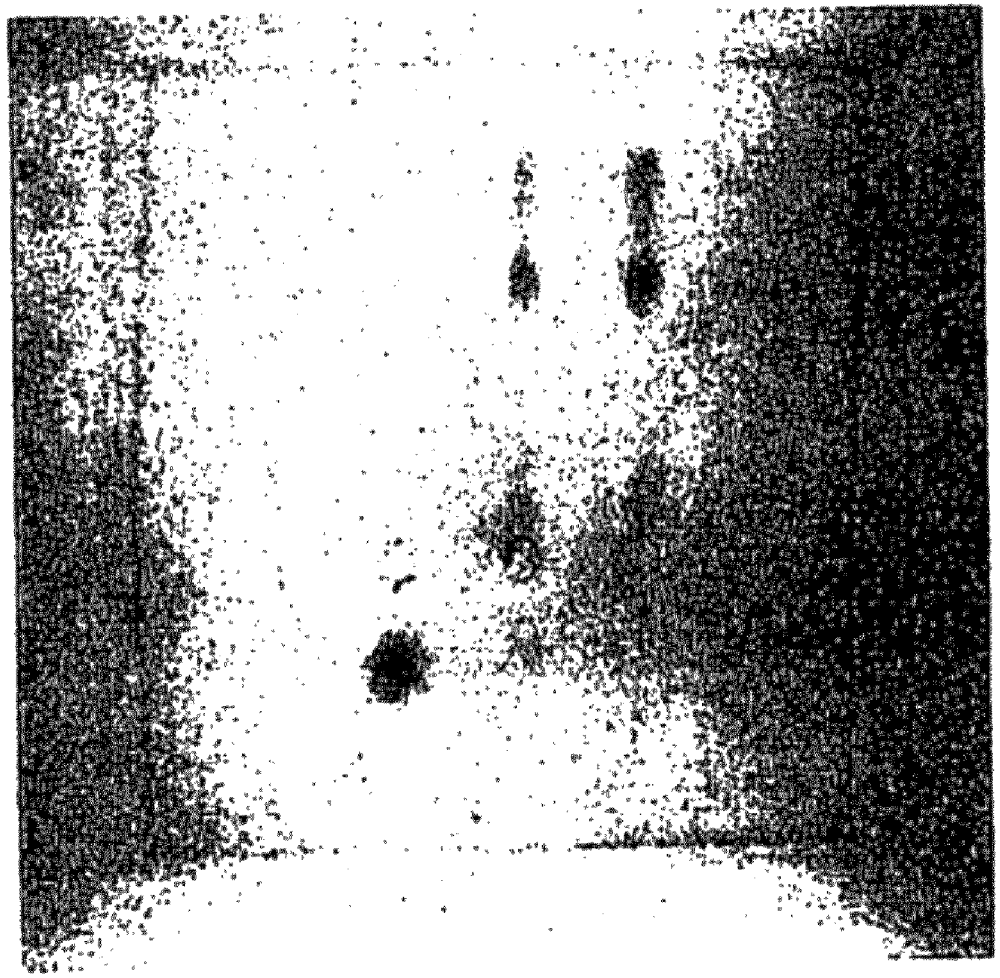
FIG. 8 is a photograph of an electrophoresis agarose gel showing bound IPF and gp41.

The peptides in the IPF fractions may be isolated and concentrated by any one of several techniques well-known to those skilled in the art, such as ammonium sulfate precipitation. The produced peptide isolate may be purified by standard processes such as gel filtration and RP-HPLC, and inactivated by exposure to a neutral-to-alkaline environment of about pH 6.5 or greater or as otherwise known in the art. The peptide may also be alkylated to increase immunogenicity if desired, for example, by the process described for methylation in U.S. Patent Application Publication US 2004/0018639 A1. A HPLC chromatogram of the purified, inactivated IPF-6 product in accordance with one embodiment of the present invention is shown in FIG. 3.

Homologues or analogues of the sequence which conserve at least critical binding site amino acid structures and functions and also conserve any distal structural/functional residues essential for binding activity as described herein may be substituted for the IPF of SEQ ID: NOS. 1-6 (IPF-1-IPF-6). Variants of the sequences, including chemically modified derivatives, having a high sequence similarity will be generally preferred, provided that binding activity is not significantly adversely affected. Residues superfluous to the disclosed function of the peptides in accordance to aspects of the present invention may be deleted or added with the same proviso. Modified sequences may be evaluated for conserved binding activity by, for example, following the binding assays described herein or in the literature. Numerous databanks are accessible for protein sequence analysis, such as those which combine sequence similarity with fold recognition to predict functional equivalents. Binding properties (affinity, specificity, etc.) may also be evaluated by the binding assays described below or other conventional assays, as known in the art.

BIACORE assays were used for binding affinity. See FIG. 6. This technology measures mass concentration of biomolecules close to a surface. The surface is made specific by attaching one of the interacting partners. Sample containing the other partner(s) flows over the surface: when molecules from the sample bind to the interactant attached to the surface, the local concentration changes and an SPR (surface plasmon resonance) response is measured. The response is directly proportional to the mass of molecules that bind to the surface. The SPR response may be expressed by resonance units (RU). One RU represents change of 0.0001 in the angle of the intensity minimum which is equivalent to a change in concentration of 1 pg/mm.

The exact conversion factor between RU and surface concentration depends on properties of the sensor surface and the nature of the molecule responsible for the concentration change. Assays tracking the binding of IPF with CD4 cells, gp41, gp120, and human sera are useful to detect the formation of the super antigen responsible for the specific immune response. That is, the high response of IPF fragments, measured in Response Units, indicates a high utility as a specific binding agent for components of HIV.

IPF-6 demonstrates binding in vitro with nonglycolysed fragment 579-601 of the HIV-1 envelope protein gp41 subunit; with gp120 HIV-1 subunit, with human CD4+ cells and with human serum under gel electrophoresis (Biocor method) (see, FIGS. 4-8). The assays for these bindings were conducted by The Institute for Molecular Medicine using standard protocols. The spontaneous binding of IPF-6 with the gp41 HIV-1 envelope glycol protein is a particularly important biological property. Separately, under simple agarose electrophoresis, IPF-6 and gp41 move in opposite directions. However, when they are mixed prior to electrophoresis, gp41 changes direction and takes the direction of IPF-6. By way of example, quantitative analysis showed that the binding capacity ratio of IPF-6 to gp41 was 1:0.66. That is, three molecules of IPF-6 bound two molecules of gp41 to form a complex which may function in vivo as, for example, a superantigen with significant anti-HIV-1 biological activity. Such antigen may be used as a bioassay reagent, in the production of mono- or polyclonal antibodies, in the manufacture of vaccines, and in other applications wherein antigens are conventionally employed.

While the mechanism of these binding events is not completely understood, it is contemplated that exposure of HIV-1 to the IPF-6 according to embodiments of the present invention will effectively block gp41 and gp120 domains essential for viral entry into CD4+ cells and inhibit viral infection, in vivo and in vitro. See, M I. Greenberg et al., *Prog. Abstr.* $8^{th}$ *Conf. Retrovirus Oppor. Infect.,* 2002 Chicago Ill., 8: 184 (abstract No. 473) and C. D. Pilcher et al., $9^{th}$ *Conf. Retroviruses and Oppor. Infect.,* Seattle, Wash., "T-20 and Beyond: Inhibition of HIV Attachment and Fusion at the $9^{th}$ CROI" (February 2002), both of which are incorporated herein by this reference. It is also contemplated that the IPF-6 in accordance with embodiments of the present invention will effectively compete with HIV-1 for its CD4+ cell surface binding sites and inhibit virus entry into these cells, in vivo and in vitro. Various in vitro protocols are known in the art for predicting in vivo antiviral activity of compounds for inhibiting replication of HIV, and these protocols may be used in connection with embodiments of the present invention. Exemplary art-recognized anti-HIV screening assays are cited in U.S. Pat. No. 5,869,522, issued 9 Feb. 1999 to Boyd et al., including those described in *J. Virol. Methods,* 33:87-100,1991; *J. Natl. Cancer Inst.,* 81:577-586, 1992; *J. Med. Chem.* 35:1978-1986, 1992, and Boyd, M. R., in *AIDS Etiology: Diagnosis, Treatment, and Prevention*, pp 305-319 (Lippincott, 1988, DeVita, V. T., Jr., et al., eds).

In accordance with one aspect of the present invention, IPF-6 is used to diagnose viral infection, particularly HIV-1 infection. Bioassays suitable for this purpose are well-known and routine. Typical of these are assays based on competitive binding between, for example, a known amount of a viral protein and a biological sample to be tested for the same viral protein, using an excess of antiviral reagent capable of specifically binding with the known protein, such as an antibody. A mixture of these is incubated and the amount of bound complex calculated and compared to that in a control mixture lacking the sample. The presence, if any, and amount of the viral protein in the sample can then be determined. There are numerous variations on this process, such as sandwich assays, assays with immobilized reagent, assays using labeled reagent (e.g., ELISA, RIA, FIA), and so on. Whatever the variation, whether for detecting or quantifying complex, or for additional reagents, or other modification, they all require a binding agent for the unknown sample. Any of these routine binding assays for quantifying or identifying an unknown sample may thus be used in the practice of embodiments of the present invention by substituting IPF-6 as the antiviral binding agent for samples to be tested for HIV-1 gp120, gp41, or infected CD4+T-cells.

In accordance with another aspect of the present invention, IPF-6 is used as a prophylactic or therapeutic to prevent or to treat HIV infections. (Herein the term "HIV infections" refers to AIDS and ARC in addition to viral infection per se unless otherwise noted). For in vivo use, the IPF compositions disclosed herein may be prepared for administration by mixing it at the desired degree of purity with a pharmaceutically-acceptable carrier suitable for the route of administration, as well-known in the art. Although the IPF compositions disclosed herein are desirably administered with an adjuvant in some applications, in situations where a series of IPF doses are administered, boosters with the respective IPF may not require adjuvant. Intramuscular or subcutaneous injections are presently the contemplated route for both therapeutic and prophylactic administration of the IPF compositions disclosed herein. However, intravenous delivery, delivery via catheter or other surgical tubing, or other parenteral route may also be used. Alternative routes include oral routes for administering tablets, liquid formulations and the like, as well as inhalation routes. Liquid formulations reconstituted from powder formulations may be utilized. The IPF compositions disclosed herein may also be administered via microspheres, liposomes, or other microparticulates, and via delivery systems or sustained release formulations dispersed in certain tissues including blood.

The dosage administered of the IPF compositions as disclosed herein will depend upon the properties of the formulation employed, e.g., its binding activity and in vivo plasma half-life, the concentration of IPF in the formulation, the administration route, the site and rate of dosage, the clinical tolerance of the patient involved, the patient's condition, and other considerations, as known in the art. Different dosages may be utilized during a series of sequential treatments. The practitioner may administer an initial dose and then boost with relatively smaller doses of IPF. The dosages of the IPF compositions disclosed herein may be combined with other HIV antivirals such as AZT.

EXAMPLES

Example 1

Preparing the IPF-HSP Complex

The IPF may be extracted and purified according to commonly owned U.S. Provisional Application No. U.S. Provisional Patent Application N. 60/644,054, filed Jan. 18, 2005, Zhabilov, entitled "Inactivated Pepsin Fraction, Pharmaceutical Compositions, and Methods for Detecting and Treating Diseases." For the HSP component, gp69 may be extracted and purified from fibrosarcoma cells as set forth in Chandawarkar, et al., "Immune modulation with high-dose heat shock protein gp96: therapy of murine autoimmune diabetes and encephalomyelitis," International Immunology, Vol. 16, No. 4, pp. 615-624 (2004). After the two components are isolated, then the gp69 may be covalently bonded to the IPF as described below.

Example 2

Efficacy of Immunizing/Vaccinating Murine Hosts Against HT29 Tumors

The IPF is isolated from lyophilized pepsin and gp96 is obtained, readily lyophilized (P14625-human tumor rejection antigen-gp96). 12 mg of IPF (6 mg per ml) and 96 μg of gp96 (48 micrograms per ml) per 2 ml vial are diluted in a buffer solution and after an incubation period of 12 hours 0.004M Sodium Caprylate and 0.004 M Sodium Acetyltryptophanate are added. The solution is maintained at a temperature of about +4 Celsius.

Two basic groups consisting of ten athymic nude mice each are tested and analyzed for tumor growth and other physiological conditions.

For Group 1, ten mice are injected with a 1 ml IPF-gp96 complex at days 1, 3, 5 and 7. Ten days after last the injection, the mice are injected with HT29 (human colorectal adenocarcinoma) cells and tumor measurements are observed for days 17 to 35.

For Group II, ten mice are injected with buffer solution at days 1, 2, 5 and 7. Ten days after the last injection, the mice are injected with HT29 cells and tumor measurements are observed for days 17 to 35.

The mice in both groups are analyzed. No melanoma cells are detected in the first group but all the mice in the second group develop melanoma cells.

Example 3

Efficacy of Therapeutically Treating Murine Hosts Against HT29 Tumors

The IPF is isolated from lyophilized pepsin and gp96 is obtained, readily lyophilized (P14625-human tumor rejection antigen-gp96). 12 mg of IPF (6 mg per ml) and 5.5 μg of gp96 (2.75 micrograms per ml) per 2 ml vial are diluted in a buffer solution and after an incubation period of 12 hours 0.004M Sodium Caprylate and 0.004 M Sodium Acetyltryptophanata are added. The solution is maintained at a temperature of about +4 Celsius.

Two basic groups consisting of ten athymic nude mice each are tested and analyzed for tumor growth and other physiological conditions.

For Group I, at day 17 from the start of the experiment, ten mice are injected with HT29 for tumor development. After five days, the mice were injected with 1 ml IPF-gp69 solution on days 22, 24, 26 and 28 cells and tumor measurements are observed for days 17 to 35.

For Group II, at day 17 from the start of experiment, ten mice are injected with HT29 for tumor development. After give days, the mice are injected with buffer solution at days 22, 24, 26 and 28 and tumor measurements are observed for days 17 to 35.

The mice in both groups are analyzed. No melanoma cells are detected in the first group but all the mice in the second group develop melanoma cells.

Example 4

For both Examples 2 and 3, the following protocol is used.
Culture of Human Cancer Cell Line:
1. Thaw out frozen (liquid nitrogen) aliquot of HT29 cells (from ATCC).
2. Disperse into 75 $cm^2$ flask containing McCoy's 5A media supplemented with 10% fetal bovine calf serum (FBS) and incubate at 37 Celsius in humidified atmosphere of 5% $CO_2$.
3. As cells become 90% confluent, expand cultures to 150 $cm^2$ flasks.
   a. Supplement or renew culture media as needed.
   b. Freeze down vials of cell line for future use (SOP #11,000).
4. Continue to expand culture until sufficient cells are available for injection into mice (i.e. $2 \times 10^6$ HT29 cells per mouse).
B. Establishment of Tumors:
1. Receive (SOP 1910, SOP 1920) 35 male Nu/Nu mice and house using filter-topped cages supplied with autoclaved bedding.
2. Note: All mouse handling procedures should be carried out in laminar flow hood to prevent contamination of animals.

3. Implantation:
 a. Ear tag mice (SOP 810) for identification purposes
 b. Record initial weight.
 c. inject cancer cells subcutaneously (SOP #1610) in both flanks, $1\times10^6$ cells/flank in 0.1 ml (DAY 17).
4. Staging:
 a. Record tumor measurements every Monday, Wednesday, and Friday for until tumor become 100 mm3.
 b. To reduce variability, the tumors will be measured by one technician.
C. Treatment Regimen
1. Treatment:
 a. Record mouse weights
 b. Record tumor measurements
 c. Sort mice into 2 treatment groups (Group 2 Therapeutic and Group 3 Vehicle) of 10 mice each based upon tumor size
 d. Start dosing regimen
2. Monitoring:
 a. Record mouse weights M, W, F.
 b. Record signs of distress daily
 c. Record tumor measurements M, W, F.
 d. Dose mice when required.

Example 5

Measurement of Immune Response

From Examples 2 and 3, immune responses are measured.
Methods of CD4 cell Determination All bloods samples are analyzed for their CD4 cell counts by flow cytometry. Triple labeling methods are utilized whereby CD45 monoclonal antibody is used to gate lymphocytes (based on their high expression of CD45 and low side scatter characteristics). Within this gate, the double positive CD3+CD4+cells are analyzed. This method of CD4 determination therefore excludes any cells (lymphocytes) which expresses only the CD4 marker.

Observation of CD4 cell

After the last injection, all of the mice from Group I (Examples 2 and 3) show a new population of CD4 cells which seem to be excluded in the routine CD4 cell flow cytometric assays of Group II (Examples 2 and 3). This is due to the fact that (as explained above) the flow cytometric method employed would exclude these cells due to their non-expression of CD3 marker. These "new" cells are apparent on a dot plot of SSC versus CD4. An intermediate population of CD4 cells which are not monocytes, and a population of brightly fluorescent CD4+population (true $T_{helper}$ cells) are observed.

Use of other monoclonal antibodies confirms these cells do not comply either to naïve or memory status (by the expression of CD45RA or CD45RO expression respectively) and they do not appear to express TCR of alpha or beta subtype.

It is proposed that these "new" cells are in fact dendritic cells which are CD4+ that are responsible for the immune regulatory activity of IPF. Such cells are known to secrete IL12 which enhances CMI to infectious organisms and swing the regulatory arm of immunity to a beneficial $T_{H1}$ phenotype. This would account (at least in part) for the other markers of immune reactivation induces by IPF, e.g., increased secretion of INF-γ by CD8 cells upon stimulation in vitro with HIV recombinant p24, improved functions of both CD4 and CD8 cells in response to a polyclonal activator and decreased in CD8+CD38+cells (bad prognosis marker) over time.

Overall a measured immune response may give evidence of two actions:

(1) Cytotoxic effect against tumor cells. Cytotoxic T lymphocytes (CTLs) are effectors CD8+ that can mediate the lyses of target cells bearing antigenic peptides associated with a MHC molecule. Other cytotoxic cells include gamma/delta chain and CD4+ NK 1.1+ cells.

(2) Increase antibody production. It could be assumed that the IPF is binding to gp96 identified as a major Epitope recognized by antibodies in the patient's body, as antigen presenting molecules, and this new super antigen stimulates immune response using a non-conventional antigen processing pathway.

From Examples 2 and 3, one or more of the following observations may be made:
 increase in the CD4+CD45 RO+CD62 L population
 increase in the CD4+CD45 RA+CD62 L population
 appearance of a second CD4+ population having lower CD4 intensity but no increase in SSC. This implies a second CD4 cells population. Preliminary analysis of this population in isolation do not reveal these cells to be memory or naïve cells.
 there is a parallel increase in absolute CD4 cell counts when this phenomenon appears.
 increase in the CD8+CCR5+population also in parallel to the above mentioned parameters.

Functional changes over time: Since some functional assays are conducted it is interesting to note the following change in parallel to the phenotypic change above:
 increase in the IFN-γ containing CD3+CD4+cells post stimulation in vitro
 decrease in the IL-4 containing CD3+CD4+cells post stimulation
 significant increase in the IFN-γ containing CD3+CD8+ cells over time.

While various embodiments of the present invention have been described above, it should be understood that they have been presented by way of example only, and not limitation. Thus, the breadth and scope of the present invention should not be limited by any of the above-described exemplary embodiments, but should instead be defined only in accordance with the following claims and their equivalents.

Example 6

Isolation and Purification of Irreversibly-Inactive Pepsin Fraction

The following Examples are examples of methods for isolating, purifying, and characterizing the IPF compositions disclosed herein from active pig pepsinogen.

Example 7

Isolation and Inactivation of Pepsinogen Fragment

All the buffers and solutions used in this section were sterilized by filtration. If needed, the buffers (0.2 N or 0.1 N HCl) were used to adjust the solutions. All the chemicals, including the distilled water, for the preparation of the buffers and solutions were USP Grade. The ratio of the pepsin to the buffers was 1:4 (weight/weight).

IPF was isolated from active pepsin (Sigma 1:10000) by ammonium sulfate precipitation with centrifugation at about 4° C. The lyophilized pepsin powder was dissolved in 0.14M sodium chloride (NaCl), 0.05M sodium acetate ($CH_3COONa.3H_2O$), 0.05M sodium citrate ($C_6H_5O_7Na_2.2H_2O$), and 0.10N HCl (pH 2.8-3.2) buffer. The pepsin is dissolved in buffer at pH 2.8-3.2 and the suspension incubated for 30 minutes at pH 3.2. The pH of the active pepsin suspension was then increased to 6.2-6.6 and the suspension was incubated for 30 minutes at pH 6.6. The suspension was then precipitated with a saturated solution of $(NH_4)_2SO_4$. After degradation, the mixture was centrifuged (8000 RPM at 4° C.) for 60 minutes and the supernatant discarded. The pellet was dissolved in a minimum quantity of 0.14M NaCl at a ratio of 1:2 (weight/weight), and the resulting solution was dialyzed for 18 hr against dialysis buffer: 0.1M NaCl, 0.1M sodium acetate, and 0.02M thimerozal USP, pH 6.8.

Example 8

Purification and Recovery of Irreversibly Inactivated Pepsinogen Fragment

The purification of IPF included the following steps: dialysis, centrifugation, gel filtration, and reversed-phase HPLC.

After dialysis, the low molecular weight dialysate was centrifuged at 15,000 rpm at 4° C. for 60 minutes (Beckman rotor) with precipitation of the residual ammonium sulfate. The product was purified by gel filtration to recover purified IPF from the crude mixture, and then purified by filtration on Bio-gel P10 or Sephadex G-75 gels (from Pharmacia Uppsala, Sweden), or 0.2µ SFCA membrane (Nalgene Labware, Rochester, N.Y.). Further purification was achieved by reversed phase high-performance liquid chromatography in an RP-HPLC system GOLD (Beckman) on C-18 columns (RP Ultrasphere 10 mm Spherical 80A Preparative 21.2×150 mm) using gradient 30% acetonitrile diluted in sterile water, HPLC-grade at 15% methanol HPLC-grade mobile phase. Detection 254 nm; flow rate 0.850 ml/min., solvent at pH 6.8. The final purification step included sterile filtration with Nalgen filters 0.45µ. The HPLC elution profile of the product showed one isolated peak, IPF (see FIG. 3).

Example 9

Determination of Molecular Weight

Molecular weight was determined by silver stained 13% non-reducing SDS-PAGE using the Laemmli method (*Nature* 227-680, 1970). The molecular weight standard demonstrated one peptide with a molecular weight of 45.000 KD (FIG. 2). This band was isolated, and HPLC chromatogram (FIG. 3) confirmed a single peptide in the band.

Example 10

Surface Plasmon Resonance (SPR) for Detection of IPF Activity

An assay based on SPR may be used to characterize the quality of different batches of IPF or other sample preparations. The BIACORE biosensor instrument for detecting compound ligand interaction. BIACORE may capture proteins including molecules from ctyosolic or tissue extracts on sensor surfaces and measure the binding kinetics. SPR is an optical technique that measures the refractive index change occurring at the sensor liquid-fluid interface layer. A plastic fluidics system plate is pressed into contact with a gold-coated glass chip (CM5), the surface of which is coated with an-un-cross-linked carboxymethylated dextran polymer matrix. The partial gold mirror is the optical port as well. Experiments may be performed by computer-driven robotics systems to facilitate consistency. The injection of analyte across a ligand immobilized in the matrix produces a real-time change in refractive index signifying an increase in associated molecular mass. IPF preparation may be the analyte which binds to the immobilized CD4 molecules. The data trace is a sensogram plotting response units (RU) against time. See FIG. 9.

Measured direct binding of an active component of IPF samples to an immobilized human CD4 molecules, which are binding receptors for HIV. Immobilization of CD4 on the CM5 sensor surface may be performed by standard amine coupling. The BIAcore system was equilibrated in running buffer (PBS, 0.05% Tween 20, 1 mM EDTA, pH 8.4) at a flow rate of 5 ml/min. The carboxymethylated dextran matrix was activated by injection of 35 ml of a solution containing NHS (0.05M)/EDC (0.2M) (50/50). Thirty-five microliters of CD4 at 500 mg/ml in citrate buffer (pH; 0.01M) was injected. The deactivation of the remaining NHS-ester groups was performed by injection of 35 ml of ethanolamine hydrochloride (pH 8.5; 1M). A regeneration of the sensor surface was done by the injection of 5 ml of IM NaCl and 0.1 M NaOH. The experiments were performed at a constant flow rate of 5 ml/min of running buffer. All the reagents are prepared by dilution in running buffer.

Example 11

Assessment of Binding Activity

Samples of IPF (#18, 19, 20, and 21) were used to detect binding with gp120, gp41, CD4+ cells, and serum from a healthy patient. New chips were coated with these proteins and Biacore assays for binding activity were performed. These samples were diluted to 1:2000, 1:500 and 1:100. The results are shown in FIGS. 4, 5, 6, and 7. Sample #21 bound to all target proteins better than the other samples. The assay used a Biacore (Biacore AB, Uppsala, Sweden) system based on sensor chips which provide surface conditions for attaching molecules of interest, a microfluidic flow system for delivering samples to the surface, and a surface plasma response (SPR) which detects mass concentration at the surface. SPR-based biosensors monitor interactions by measuring the mass of molecules bound to the surface. This response is expressed by resonance units (RU), whereby a change in concentration of 1 pg/mm is equivalent to a change of 0.0001 in the angle of intensity minimum, which equals one RU. The exact conversion factor between RU depends upon the properties of the sensor surface and the nature of the molecule responsible for the change in concentration. The assays demonstrate the formation of superantigen for provoking immune response.

Example 12

UV Absorption

Circular dichroism (CD) provides information about the secondary structure of optically active materials. The far-UV or amide region (170-250 nm) is dominated by contributions of the peptide bonds, whereas CD bands in the near-UV region (250-300 nm) originate from the aromatic amino acids. The UV region of IPF was in the range of 252-260 nm.

Example 13

Methylation of IPF

The purified IPF was methylated to form a methylated IPF preparation as follows. IPF was mixed with CH2BrCOOH in sufficient quantity to produce a final solution of 0.2 M CH2BrCOOH. For example, 2.78 g CH2BrCOOH was dissolved in 10 ml distilled water and added to 100 ml IPF from the HPLC purification step, containing 700 mg IPF (7 mg/ml). The pH of the mixture was adjusted to and maintained at 7.2 with 0.1M NaOH. The mixture was allowed to incubate from 6 to 8 hours. The IPF protein in the resulting aqueous fragment was concentrated by ammonium sulfate precipitation, using techniques known in the art. To 10 ml of the methylated IPF was added an equal is volume of saturated ammonium sulfate. The mixture was refrigerated at 4° C. for 12 hours and then centrifuged at 15000 rpm for 60 minutes. The pellet was removed and dissolved in final buffer containing 0.1M NaCl, 0.1M sodium citrate, and 0.02M thiodiglycol. The mixture was then dialyzed against the same buffer, to remove ammonium sulfate, for 24 hours.

Methylated IPF is lyophilized to form a slightly yellow powder. It is stable at room temperature but is preferably stored under refrigeration. The molecular weight of the IPF fragment was determined by silver stained 13% non-reducing SDS-PAGE (sodium dodecyl sulfate-polyacrylamide gel electrophoresis) using the Laemmli method (Laemmli, U.K., Nature, 227:680 (1970)). Standards were: bovine serum albumin (66,000 molecular weight, MW); porcine heart fumarose (48,500 MW); bovine erythrocytes carbonic anhydrase (29,000 MW); bovine milk beta-lactoglobulin (18,400 MW); and bovine milk α-lactalbumin (14,200 MW). The isoelectric point of the IPF composition is about 6.2 as determined by isoelectric focusing. Pepsin, in contrast, has a low pI.

Example 14

Adjuvant

The IPF may be formulated in an aluminum hydroxide adjuvant. 1 ml of an IPF formulation may contain: about 4 mg IPF, about 0.016 M AlP0$_4$ (or about 0.5 mg Al$^{3+}$), about 0.14 M NaCl, 0.004 M CH.$_3$COONa, about 0.004 M KCl, pH 6.2. ALUM-aluminum hydroxide; Al (OH) 3. Aluminum hydroxide is a widely used adjuvant, especially in commercial products such as vaccines. It is very well suited for strong antigens. Many sources of aluminum hydroxides are available, e.g. Alhydrogel, Accurate Chemical & Scientific Co., Westbury, N.Y.

Example 15

Preparation of IPF Injection for Treating HIV

The inactivated pepsin fragment suspension may be prepared for injecting a preparation of highly purified inactivated pepsin fragment, such as the IPF-6 fragment with a molecular weight of 45 KDa.

For example, the formulation may comprise (w/v) 0.4% inactivated pepsin fragment, 0.23% aluminum phosphate U.S.P., 1.29% sodium citrate U.S.P., 0.41% sodium acetate U.S.P. and water for injection to 100%. For a 1000 ml batch: place 900 ml of U.S.P. sterile water into container, preferably glass. Add 12.9 g sodium citrate and mix until dissolved. Add 4.1 sodium acetate and mix until dissolved. Add 4 g inactivated pepsin fragment, mix until a homogenous clear solution is obtained. Filter the resulting solution through a sterile 02. µm filter into a sterile depyrogenated 2 liter container with a sterile magnetic stirrer. Sterile filter 55 ml of 0.016 M trisodium phosphate solution into the above 2 liter sterile container. Sterile filter 50 ml of 0.016 M aluminum chloride solution into the 2 liter container, with the aluminum chloride being dispensed at a steady, drop by drop rate. Stir the resulting inactivated pepsin fragment suspension for 30 minutes at room temperature. Continue stirring for another 6 hours at 4° C. The sterile inactivated pepsin fragment suspension is ready to be filled into sterile 3 ml borosilicate vials.

The final 1 ml of the final IPF formulation may contain: 4 mg IPF (purity preferably >96%±0.290); 2.26 mg 0.016M AlPO$_4$ (or 0.5 mg Al$^{+3}$); 4.1 mg 0.004M CH$_3$COONa (sodium acetate); and 12.9 mg C$_6$H$_5$O$_7$ (sodium citrate); pH 6.2. In yet a further embodiment, the formulation may comprise per vial, about 8 mg IPF, 4.52 mg aluminum phosphate, 1.0 mg aluminum, 25.8 mg sodium citrate and 8.2 mg sodium acetate. In one regimen, 2 ml of this formulation makes up one vial with the dosage per patient per day being 16 vials. During the regimen, the patient should be monitored to assess the effectiveness of the regimen. CD+4 cell counts are useful and common methodology for evaluating HIV infection, as are assays for antibody or T-cell titers.

Example 16

Laboratory Results from IPF-Treated Patients

1. Increase in WBC after the second week of treatment
2. Two times increase in MHC II cell expression as well as an increase in HLA-DR receptor expression after the first week of treatment
3. Increase in gamma/delta chain expression on T-cells after the second week of the treatment and their decrease after fourth weeks
4. Drop in CD4 cells count after second week and gradual, uninterrupted increase after the third week
5. Dramatic increase in HIV-1 RNA by pcr the second week
6. Two times increasing in IgG after the forth week
7. Two to ten times increases in HIV-1 antibodies after the forth week measured by Western Blot
8. Serum conversion from p24 positive to p24 negative
9. One to two log decreases in HIV-1 RNA by per, becoming to undetectable one month after the end of the treatment
10. Reduction of HIV-1 infected cells' population as measured by PBMC's to undetectable.

The results of the above blood investigation may be interpreted as:

1. Increasing in WBC shows cell stimulation by IPF
2. Increasing in MHC II and HLA-DR receptor expression verifies that the IPF is being recognized
3. Increasing in gamma/delta expression demonstrates activation of the T-cells antigen receptors. Gamma/delta T-cell receptors share many cell-surface with alpha/beta T-cells and are able to secret lymphokines and express cytolytic activities in response to antigen stimulation.
4. CD4 decreasing after the second week suggest cytolytic activity against CD4 HIV-1 contaminated cells. This observation provides explanation why there is an increase of the serum viral load after the third week
5. The most important result from the IPF treatment is a specific anti HIV-1 antibody increasing in high level. It may be assumed that the IPF introduced in human body strong links with gp41 HIV-1 envelop protein and new billed-up superantigen after antigen processing elicits antibody production in sufficient quantity to eliminate the viral infection.

Example 17

Observations of Immunological Changes in Select Patients from Example 16 During Follow Up The study was placebo-controlled and double blind, thus the changes reported hereunder cannot be directly linked to patients who may be receiving the active investigational compound. However, it is plausible that the immunological changes detected in the lymphocytes of these patients may be induced by the IPF.

A. Phenotypic Changes in Whole Bloods:

It is apparent from the follow up samples of patients when analyzed on the flow cytometer that significant and sustainable changes occur in certain subsets of lymphocytes. These changes are observed following the period of active therapy (ie. After day 51 onwards). Once detected, these changes are sustained over time. Such changes include:

a) Increase in the CD4+CD45RO+CD62L population
   b) Increase in the CD4+CD45RA+CD62L population
   c) Appearance of a second CD4+ population having lower CD4 intensity but no increase in SSC: this implies a second CD4 cell population. Preliminary analysis of this population in isolation does not reveal these cells to be memory or naïve cells.
   d) There is a parallel increase in the absolute CD4 cell counts when this phenomenon appears.
   e) Increase in the CD8+CCR5+ population also in parallel to the above-mentioned parameters.

B. Functional Changes Over Time:

Since some functional assays are conducted, it is interesting to note the following changes (in parallel to the phenotypic changes cited above):

a) Increase in the IFN-γ containing CD3+CD4+ cells post stimulation using p24 in vitro.
   b) Decrease in the IL4 containing CD3+CD4+ cells post stimulation
   c) Significant increase in the IFN-γ containing CD3+CD8+ cells over time.

All patients were in the active arm of the study. If so, then it would seem plausible that IPF induces a shift in the cytokine profiles in response to the virus. This 'shift' would be to a more beneficial TH1 mediated response and in so doing, indirectly enhancing the activity of the virus-specific CD8 cells and their cytotoxicity. IN parallel, there would be viral control and recovery of the immunological elements (memory cells, etc).

Example 18

Immunological Results of Clinical Trials Showing Action of IPF

1. Increase in percentages and numbers of CD8, CCR5 positive cells in treated patients.
2. Significant decline in CD8+, CD38+ cells in treated patients.
3. Significant increase in both CD4+ iNFg secreting cells in the treated patients.

Example 19

IPF Formulation and Administration

The following is an example of a contemplated IPF formulation, dosage and administration schedule, which may be used with the IPF compositions disclosed herein:

The patient is administered an intramuscular injection containing 8 mg of the IPF composition (preferably 2 ml of a formulation containing 6 mg/ml of IPF in a pharmaceutically acceptable solution) or 57 μg of IPF protein per kg body weight of the patient. Each treatment course consists of 16 injections, with two injections on consecutive days per week for 8 weeks. Three months after the last injection, if the patient's condition warrants, the treatment regimen is repeated. The treatment regimen may be repeated until satisfactory results are obtained, e.g., a halt or delay in the progress of the infection or disease, an alleviation of the infection or disease, or a cure is obtained. Preferably, in this application, IPF will be formulated with an aluminum hydroxide adjuvant.

Example 20

Treatment of Pancreatic Carcinoma

Table 1 includes data from a preliminary study of a 54 year-old male patient with $4^{th}$ stage pancreatic carcinoma treated with two cycles of treatment with IPF, which were administered to the patient in September, 2008. Unenhanced images of the liver were obtained at 5 mm interval and thickness. Following bolus of IV infusion of 125 ml of nonionic contrast (Isovue 370) parameters used were: abdomen and pelvis 5 mm thick helical scans; axial reconstructions were obtained at 2.5 mm slice thickness and 2 mm slice interval; patient received oral contast. Prior examination was on Apr. 18, 2008. In this study, the full treatment comprises three cycles of 16 vials of IPF each cycle.

In the second examination, tumor measurement was obtained with a CT scan done in November 2008. CT scan of the abdomen with limited imaging through the lower lungs showed that the patient had two very small focal densities in the right middle lobe likle atelectasis. No pleural effusion were seen. In the liver is significant for multiple hypodense lesions consistent with metastases. Many of these appear to decrease slightly in size when compared to the prior examination. The lesion in the posterior right lobe currently measures 35×22 mm. Previously it measured 43×33 mm. A lesion in the anterior left lobe currently measures 18×17 mm. previously it measured 26×25. The other lesions all appeared to decrease in size. There was a hypodense lesion seen in the spleen slightly decreased consistent with a metastatic lesion. The pancreatic mass was not well demonstrated due to adjacent stomach. It measured approximately 40×48 mm slightly decreased in size. The patient has had a prior cholecystectomy. Left adrenal masses were demonstrated suggesting metastases not significantly changed. The kidneys showed normal excretion of contrast bilaterally. A large amount of ascites is present new compared with prior examination.

No definite retroperitoneal lymphadenopathy or pelvic lympadenopathy was demonstrated. Two small focal right middle lobe lung densities were likely atelectasis. Multiple hypodense lesions consistent with metastases all were slightly decreased when compared with the prior examination. Splenic lesion had decreased. Left adrenal masses not significantly changed. Large amount of ascites present new. Pancreatic mass poorly demonstrated bu likely slightly decreased. The finding on the CT scan showed that most of the lesion in the liver, pancreas and spleen had decreased in size. The patient's CA 19-9 at 19, returned to normal.

The IPF composition used in this study comprised IPF-IL2 adjuvant, specifically the study was done using SEQ ID: NOS. 1 and 2. The Roche Modular E170 CA 19-9 electrochemiluminescent immunoassay was used.

TABLE 1

| Date | Cancer Antigen 19-9, U/mL (ref range: 0-37 U/mL) | Alkaline Phosphatase, U/L (ref range: 38-126) |
|---|---|---|
| Jan. 15, 2008 | 31 | 101 |
| Mar. 07, 2008 | 52 | 143 |
| Mar. 27, 2008 | 116 | * |
| Apr. 24, 2008 | 97 | 235 |
| May 07, 2008 | 52 | * |
| Jun. 03, 2008 | 108 | 133 |
| Jul. 15, 2008 | 68 | 141 |
| Aug. 05, 2008 | 55 | 207 |
| Oct. 07, 2008 | 22 | 95 |
| Nov. 12, 2008 | 19 | 103 |

A person skilled in the art would appreciate that exemplary embodiments described hereinabove are merely illustrative of the general principles of the present invention. Other modifications or variations may be employed that are within the scope of the invention. Thus, by way of example, but not of limitation, alternative configurations may be utilized in accordance with the teachings herein. Accordingly, the drawings and description are illustrative and not meant to be a limitation thereof.

Moreover, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Thus, it is intended that the invention cover all embodiments and variations thereof as long as such embodiments and variations come within the scope of the appended claims and their equivalents.

What is claimed is:

1. An method of modulating immune activity comprising administering to a patient an effective amount of a composition comprising an inactivated pepsin fragment (IPF).

2. The method of claim 1, wherein the inactivated pepsin fragment (IPF) comprising the amino acid sequence of SEQ ID: NO. 1.

3. The method of claim 2, wherein modulating immune function comprises conferring immunity against malignant human cancer cells, and comprising the step of administering to a patient a composition comprising SEQ ID: NO. 1 combined with IL-2.

* * * * *